US006558948B1

(12) United States Patent
Kochanek et al.

(10) Patent No.: US 6,558,948 B1
(45) Date of Patent: May 6, 2003

(54) PERMANENT AMNIOCYTIC CELL LINE, ITS PRODUCTION AND USE FOR THE PRODUCTION OF GENE TRANSFER VECTORS

(76) Inventors: Stefan Kochanek, Werthmann Str. 24, D-50935 Köln (DE); Gudrun Schiedner, Nelken Str. 16, D-50733 Köln (DE)

( * ) Notice: Subject to any disclaimer, the term of this patent is extended or adjusted under 35 U.S.C. 154(b) by 0 days.

(21) Appl. No.: 09/714,550

(22) Filed: Nov. 16, 2000

Related U.S. Application Data
(60) Provisional application No. 60/167,439, filed on Nov. 23, 1999.

(51) Int. Cl.[7] ............................ C12N 5/00; C12P 21/06; C12P 21/04
(52) U.S. Cl. ...................... 435/325; 435/69.1; 435/70.1; 435/366; 435/372; 435/320.1; 424/233.1
(58) Field of Search ............................... 435/69.1, 70.1, 435/325, 366, 372, 320.1; 424/233.1

(56) References Cited

FOREIGN PATENT DOCUMENTS

| WO | WO 94/28152 | 12/1994 |
| WO | WO 97/00326 | 1/1997 |
| WO | WO 00/70071 | 11/2000 |

OTHER PUBLICATIONS

Leiden Muscular Dystrophy pages©, Leiden University Medical Center [online, retrieved Mar. 20, 2002], Retrieved from the Internet: <http://www.dmd.nl.myod.html>.*
Byrd et al., "Malignant Transformation of Human Embryo Retinoblasts by Cloned Adenovirus 12 DNA," *Nature* 298:69–71, (1982).

European Patent Application No. 99201545.3, "Adenovirus Derived Gene Delivery Vehicles Comprising at least One Element of Adenovirus Type 35," Filed May 17, 1999.
Fallaux et al., "Characterization of 911: A New Helper Cell Line for the Titration and Propagation of Early Region 1–Deleted Adenoviral Vectors," *Human Gene Therapy* 7:215–222 (1996).
Fallaux et al., "New Helper Cells and Matched Early Region 1–Deleted Adenovirus Vectors Prevent Generation of Replication–Competent Adenoviruses," *Human Gene Therapy* 9:1909–1917 (1998).
Gaffney et al., "Two Distinct Types of SV40–Transformed Human Amnion Cells," *Cancer Research* 30:871–879 (1970).
Gallimore et al., "Studies on Adenovirus Type–12 E1 Region: Gene Expression, Transformation of Human and Rodent Cells, and Malignancy," *Cancer Cells* 4:339–348 (1986).
Gallimore et al., "Transformation of Human Embryo Retinoblasts with Simian Virus 40, Adenovirus and Oncogenes," *Anticancer Research* 6:499–508 (1986).

(List continued on next page.)

Primary Examiner—Hankyel T. Park
Assistant Examiner—Stacy S. Brown
(74) Attorney, Agent, or Firm—Clark & Elbing LLP

(57) ABSTRACT

The invention relates to a permanent amniocytic cell line comprising at least one nucleic acid which brings about expression of the gene products of the adenovirus E1A and E1B regions. The present invention further relates to the production of a permanent amniocytic cell line and to its use for producing gene transfer vectors and/or adenovirus mutants. Further aspects are the use of amniocytes and of the adenoviral gene products of the E1A and E1B regions for producing permanent amniocytic cell lines.

24 Claims, 8 Drawing Sheets

OTHER PUBLICATIONS

Graham et al., "Characteristics of a Human Cell Line Transformed by DNA from Human Adenovirus Type 5," *J. Gen. Virol.* 36:59–72 (1977).

Plouzek and Chou, "Isolation and Characterization of a Human Amnion Epithelial Cell Line that Expresses the Pregnancy–Specific β1–Glycoprotein Gene," *Endocrinology* 129:950–958 (1991).

Sack, "Human Cell Transformation by Simian Virus 40—A Review," In Vitro 17:1–19 (1981).

Schiedner et al., "Efficient Transformation of Primary Human Amniocytes by E1 Functions of Ad5: Generation of New Cell Lines for Adenoviral Vector Production," *Human Gene Therapy* 11:2105–2116 (2000).

Walen and Arnstein, "Induction of Tumorigenesis and Chromosomal Abnormalities in Human Amniocytes Infected with Simian Virus 40 and Kirsten Sarcoma Virus," In Vitro *Cell. Dev. Biol.* 22:57–65 (1986).

Whittaker et al., "Isolation and Characterization of Four Adenovirus Type 12– Transformed Human Embryo Kidney Cell Lines," *Molecular and Cellular Biology* 4:110–116 (1984).

* cited by examiner

FIG. 4

| Cell line | Production (bfu/cell) | | plaques |
|---|---|---|---|
| | 24-well plate | cell culture dish | |
| GS.A55.C1 | 1300 | | |
| .E6 | 1840 | | 3 |
| .C12 | 790 | | |
| GS.N24.C3 | 380 | | |
| .C10 | 400 | | |
| .G5 | 230 | | |
| GS.N27.H9 | 1160 | 150 | 1.5 |
| .H11 | 780 | | |
| .D12 | 360 | | |
| GS.N49.C2 | 200 | | |
| .C5 | 120 | | |
| .D7 | 300 | | |
| GS.N51.D2 | 280 | | |
| .G5 | 350 | | |
| .C5 | 1140 | | 1 |
| GS.N52.C9 | 2100 | 2000 | 10 |
| .E12 | 1320 | | 18 |
| .E6 | 3150 | 2700 | 25.5 |
| .F4 | 3880 | 2400 | 6 |
| .H12 | 1640 | | 1 |
| GS.N53.G9 | 460 | | |
| .G1 | 380 | | |
| .F7 | 330 | | |
| 293 | 2370 | 2500 | 27 |

SEQUENCE LISTING

<160> NUMBER OF SEQ ID NOS: 18

<210> SEQ ID NO 1
<211> LENGTH: 513
<212> TYPE: DNA
<213> ORGANISM: Mus musculus

<400> SEQUENCE: 1

```
gaattctacc gggtagggga ggcgcttttc ccaaggcagt ctggagcatg cgctttagca      60
gccccgctgg cacttggcgc tacacaagtg gcctctggcc tcgcacacat tccacatcca     120
ccggtaggcg ccaaccggct ccgttctttg gtggcccctt cgcgccacct tctactcctc     180
ccctagtcag gaagttcccc cccgcccgc agctcgcgtc gtgcaggacg tgacaaatgg     240
aagtagcacg tctcactagt ctcgtgcaga tggacagcac cgctgagcaa tggaagcggg     300
taggcctttg gggcagcggc caatagcagc tttgctcctt cgctttctgg gctcagaggc     360
tgggaagggg tgggtccggg ggcgggctca ggggcgggct caggggcggg gcgggcgccc     420
gaaggtcctc cggaggcccg gcattctcgc acgcttcaaa agcgcacgtc tgccgcgctg     480
ttctcctctt cctcatctcc gggcctttcg acc                                  513
```

<210> SEQ ID NO 2
<211> LENGTH: 337
<212> TYPE: DNA
<213> ORGANISM: Artificial Sequence
<220> FEATURE:
<223> OTHER INFORMATION: primer

<400> SEQUENCE: 2

```
gagtgccagc gagtagagtt ttctcctccg agccgctccg acaccgggac tgaaaatgag      60
acatattatc tgccacggag gtgttattac cgaagaaatg gccgccagtc ttttggacca     120
gctgatcgaa gaggtactgg ctgataatct tccacctcct agccattttg aaccacctac     180
ccttcacgaa ctgtatgatt tagacgtgac ggcccccgaa gatcccaacg aggaggcggt     240
tcgcagatt tttcccgact ctgtaatgtt ggcggtgcag gaagggattg acttactcac     300
ttttccgccg gcgcccggtt ctccggagcc gcctcac                              337
```

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3

```
atcgagtgcc agcgagtaga gttttctcc                                        29
```

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4

```
gtgaggcggc tccggagaac cg                                               22
```

<210> SEQ ID NO 5
<211> LENGTH: 216
<212> TYPE: DNA
<213> ORGANISM: Artificial Sequence
<220> FEATURE:
<223> OTHER INFORMATION: primer

<400> SEQUENCE: 5

```
ctcgcggatc cagatctgga aggtgctgag gtacgatgag acccgcacca ggtgcagacc      60
ctgcgagtgt ggcggtaaac atattaggaa ccagcctgtg atgctggatg tgaccgagga     120
gctgaggccc gatcacttgg tgctggcctg cacccgcgct gagtttggct ctagcgatga     180
agatacagat tgaggtactg aaatggaatt ccggtc                               216
```

<210> SEQ ID NO 6
<211> LENGTH: 32
<212> TYPE: DNA
<213> ORGANISM: Artificial Sequence
<220> FEATURE:
<223> OTHER INFORMATION: primer

<400> SEQUENCE: 6

```
gacgccaatt ccatttcagt acctcaatct gt                                    32
```

<210> SEQ ID NO 7
<211> LENGTH: 31
<212> TYPE: DNA
<213> ORGANISM: Artificial Sequence
<220> FEATURE:
<223> OTHER INFORMATION: primer
```

<400> SEQUENCE: 7
ctcgcggatc cagatctgga aggtgctgag g                                          31

<210> SEQ ID NO 8
<211> LENGTH: 782
<212> TYPE: DNA
<213> ORGANISM: Artificial Sequence
<220> FEATURE:
<223> OTHER INFORMATION: primer

<400> SEQUENCE: 8
cgactgaatt caattttta a gtgtataatg tgttaaacta ctgattctaa ttgtttgtgt          60
attttagatt ccaacctatg gaactgatga atgggagcag tggtggaatg cctttaatga        120
ggaaaacctg ttttgctcag aagaaatgcc atctagtgat gatgaggcta ctgctgactc        180
tcaacattct actcctccaa aaagaagag aaaggtagaa gaccccaagg actttccttc         240
agaattgcta gttttttga gtcatgctgt gtttagtaat agaactcttg cttgctttgc         300
tatttacacc acaaaggaaa aagctgcact gctatacaag aaaattatgg aaaaatattc        360
tgtaaccttt ataagtaggc ataacagtta taatcataac atactgtttt ttcttactcc        420
acacaggcat agagtgtctg ctattaataa ctatgctcaa aaattgtgta cctttagctt        480
tttaatttgt aaagggggtta ataaggaata tttgatgtat agtgccttga ctagagatca       540
taatcagcca taccacattt gtagaggttt tacttgcttt aaaaaacctc ccacacctcc        600
ccctgaacct gaaacataaa atgaatgcaa ttgttgttgt taacttgttt attgcagctt        660
ataatggtta caaataaagc aatagcatca caaatttcac aaataaagca ttttttttcac      720
tgcattctag ttgtggtttg tccaaactca tcaatgtatc ttatcatgtc tggatccgtc        780
ga                                                                        782

<210> SEQ ID NO 9
<211> LENGTH: 32
<212> TYPE: DNA
<213> ORGANISM: Artificial Sequence
<220> FEATURE:
<223> OTHER INFORMATION: primer

<400> SEQUENCE: 9
cgactgaatt caattttta a gtgtataatg tg                                      32

<210> SEQ ID NO 10
<211> LENGTH: 27
<212> TYPE: DNA
<213> ORGANISM: Artificial Sequence
<220> FEATURE:
<223> OTHER INFORMATION: primer

<400> SEQUENCE: 10
tcgacggatc cagacatgat aagatac                                              27

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ccttgtaccg gaggtgatcg                                                      20

```
<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tggcgcctgc tatcctgaga                                              20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
tacatctgac ctcatggagg                                              20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
caagaatcgc ctgctactgt                                              20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
ggctgcagcc aggggatgat                                              20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
agggttcggg gctgtgcctt                                              20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
cctgaacggg gtgtttgaca                                              20

<210> SEQ ID NO 18
<211> LENGTH: 7090
<212> TYPE: DNA
<213> ORGANISM: Plasmid STK146
```

<400> SEQUENCE: 1

```
gtggcacttt tcgggaaat gtgcgcggaa cccctatttg tttatttttc taaatacatt      60
caaatatgta tccgctcatg agacaataac cctgataaat gcttcaataa tattgaaaaa     120
ggaagagtat gagtattcaa catttccgtg tcgcccttat tcccttttt gcggcatttt    180
gccttcctgt ttttgctcac ccagaaacgc tggtgaaagt aaaagatgct gaagatcagt     240
tgggtgcacg agtgggttac atcgaactgg atctcaacag cggtaagatc cttgagagtt     300
ttcgccccga agaacgtttt ccaatgatga gcacttttaa agttctgcta tgtggcgcgg     360
tattatcccg tattgacgcc gggcaagagc aactcggtcg ccgcatacac tattctcaga     420
atgacttggt tgagtactca ccagtcacag aaaagcatct tacggatggc atgacagtaa     480
gagaattatg cagtgctgcc ataaccatga gtgataacac tgcggccaac ttacttctga     540
caacgatcgg aggaccgaag gagctaaccg cttttttgca caacatgggg gatcatgtaa     600
ctcgccttga tcgttgggaa ccggagctga atgaagccat accaaacgac gagcgtgaca     660
ccacgatgcc tgtagcaatg gcaacaacgt tgcgcaaact attaactggc gaactactta     720
ctctagcttc ccggcaacaa ttaatagact ggatggaggc ggataaagtt gcaggaccac     780
ttctgcgctc ggcccttccg gctggctggt ttattgctga taaatctgga gccggtgagc     840
gtgggtctcg cggtatcatt gcagcactgg ggccagatgg taagccctcc cgtatcgtag     900
ttatctacac gacggggagt caggcaacta tggatgaacg aaatagacag atcgctgaga     960
taggtgcctc actgattaag cattggtaac tgtcagacca agtttactca tatatacttt    1020
agattgattt aaaacttcat ttttaattta aaaggatcta ggtgaagatc cttttttgata    1080
atctcatgac caaaatccct aacgtgagt tttcgttcca ctgagcgtca gaccccgtag    1140
aaaagatcaa aggatcttct tgagatcctt ttttctgcg cgtaatctgc tgcttgcaaa     1200
caaaaaaacc accgctacca gcggtggttt gtttgccgga tcaagagcta ccaactcttt     1260
ttccgaaggt aactggcttc agcagagcgc agataccaaa tactgtcctt ctagtgtagc    1320
cgtagttagg ccaccacttc aagaactctg tagcaccgcc tacatacctc gctctgctaa    1380
tcctgttacc agtggctgct gccagtggcg ataagtcgtg tcttaccggg ttggactcaa    1440
gacgatagtt accggataag gcgcagcggt cgggctgaac ggggggttcg tgcacacagc    1500
ccagcttgga gcgaacgacc tacaccgaac tgagatacct acagcgtgag ctatgagaaa    1560
gcgccacgct tcccgaaggg agaaaggcgg acaggtatcc ggtaagcggc agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740
tatggaaaaa cgccagcaac gcggcctttt tacggttcct ggccttttgc tggccttttg    1800
ctcacatgtt ctttcctgcg ttatcccctg attctgtgga taaccgtatt accgcctttg    1860
agtgagctga taccgctcgc cgcagccgaa cgaccgagcg cagcgagtca gtgagcgagg    1920
aagcggaaga gcgcccaata cgcaaaccgc ctctccccgc gcgttggccg attcattaat    1980
gcagctggca cgacaggttt cccgactgga aagcgggcag tgagcgcaac gcaattaatg    2040
tgagttagct cactcattag gcaccccagg ctttacactt tatgcttccg gctcgtatgt    2100
tgtgtggaat tgtgagcgga taacaatttc acacaggaaa cagctatgac catgattacg    2160
ccaagcgcgc aattaaccct cactaaaggg aacaaaagct gggtaccggg ccccccctcg    2220
aggtcatcga attctaccgg gtaggggagg cgcttttccc aaggcagtct ggagcatgcg    2280
ctttagcagc cccgctggca cttggcgcta cacaagtggc ctctggcctc gcacacattc    2340
```

```
cacatccacc ggtaggcgcc aaccggctcc gttctttggt ggcccttcg cgccaccttc    2400 tactcctccc ctagtcagga agttcccccc cgccccgcag ctcgcgtcgt gcaggacgtg    2460
acaaatggaa gtagcacgtc tcactagtct cgtgcagatg gacagcaccg ctgagcaatg    2520
gaagcgggta ggcctttggg gcagcggcca atagcagctt tgctccttcg ctttctgggc    2580
tcagaggctg ggaaggggtg ggtccggggg cgggctcagg ggcgggctca ggggcggggc    2640
gggcgcccga aggtcctccg gaggcccggc attctcgcac gcttcaaaag cgcacgtctg    2700
ccgcgctgtt ctcctcttcc tcatctccgg gcctttcgac cagcttgata tcgagtgcca    2760
gcgagtagag ttttctcctc cgagccgctc cgacaccggg actgaaaatg agacatatta    2820
tctgccacgg aggtgttatt accgaagaaa tggccgccag tcttttggac cagctgatcg    2880
aagaggtact ggctgataat cttccacctc ctagccattt tgaaccacct acccttcacg    2940
aactgtatga tttagacgtg acggcccccg aagatcccaa cgaggaggcg gtttcgcaga    3000 ttttcccga ctctgtaatg ttggcggtgc aggaagggat tgacttactc acttttccgc     3060
cggcgcccgg ttctccggag ccgcctcacc tttcccggca gcccgagcag ccggagcaga    3120
gagccttggg tccggtttct atgccaaacc ttgtaccgga ggtgatcgat cttacctgcc    3180
acgaggctgg cttccacccc agtgacgacg aggatgaaga gggtgaggag tttgtgttag    3240
attatgtgga gcaccccggg cacggttgca ggtcttgtca ttatcaccgg aggaatacgg    3300
gggacccaga tattatgtgt tcgctttgct atatgaggac ctgtggcatg tttgtctaca    3360
gtaagtgaaa attatgggca gtgggtgata gagtggtggg tttggtgtgg taatttttt     3420 tttaatttt  acagttttgt ggtttaaaga attttgtatt gtgatttttt taaaaggtcc    3480
tgtgtctgaa cctgagcctg agcccgagcc agaaccggag cctgcaagac ctacccgccg    3540
tcctaaaatg gcgcctgcta tcctgagacg cccgacatca cctgtgtcta gagaatgcaa    3600
tagtagtacg gatagctgtg actccggtcc ttctaacaca cctcctgaga tacacccggt    3660
ggtcccgctg tgccccatta aaccagttgc cgtgagagtt ggtgggcgtc gccaggctgt    3720
ggaatgtatc gaggacttgc ttaacgagcc tgggcaacct ttggacttga gctgtaaacg    3780
ccccaggcca taaggtgtaa acctgtgatt gcgtgtgtgg ttaacgcctt tgtttgctga    3840
atgagttgat gtaagtttaa taagggtga gataatgttt aacttgcatg gcgtgttaaa     3900
tggggcgggg cttaaagggt atataatgcg ccgtgggcta atcttggtta catctgacct    3960
catggaggct gggagtgtt tggaagattt ttctgctgtg cgtaacttgc tggaacagag     4020
ctctaacagt acctcttggt tttggaggtt tctgtggggc tcatcccagg caaagttagt    4080
ctgcagaatt aaggaggatt acaagtggga atttgaagag cttttgaaat cctgtggtga    4140
gctgtttgat tctttgaatc tgggtcacca ggcgcttttc caagagaagg tcatcaagac    4200
tttggatttt tccacaccgg ggcgcgctgc ggctgctgtt gctttttga gttttataaa     4260 ggataaatgg agcgaagaaa cccatctgag cgggggtac ctgctggatt ttctggccat     4320
gcatctgtgg agagcggttg tgagacacaa gaatcgcctg ctactgttgt cttccgtccg    4380
cccggcgata ataccgacgg aggagcagca gcagcagcag gaggaagcca ggcggcggcg    4440
gcaggagcag agcccatgga acccgagagc cggcctggac cctcgggaat gaatgttgta    4500
caggtggctg aactgtatcc agaactgaga cgcattttga caattacaga ggatgggcag    4560
gggctaaagg gggtaaagag ggagcggggg cttgtgagg ctacagagga ggctaggaat     4620 ctagcttta gcttaatgac cagacaccgt cctgagtgta ttacttttca acagatcaag    4680
gataattgcg ctaatgagct tgatctgctg gcgcagaagt attccataga gcagctgacc    4740
```

| | |
|---|---|
| acttactggc tgcagccagg ggatgatttt gaggaggcta ttagggtata tgcaaaggtg | 4800 |
| gcacttaggc cagattgcaa gtacaagatc agcaaacttg taaatatcag gaattgttgc | 4860 |
| tacatttctg ggaacggggc cgaggtggag atagatacgg aggataggt ggcctttaga | 4920 |
| tgtagcatga taaatatgtg gccggggtg cttggcatgg acgggtggt tattatgaat | 4980 |
| gtaaggttta ctggccccaa ttttagcggt acggttttcc tggccaatac caaccttatc | 5040 |
| ctacacggtg taagcttcta tgggtttaac aatacctgtg tggaagcctg gaccgatgta | 5100 |
| agggttcggg gctgtgcctt ttactgctgc tggaagggg tggtgtgtcg ccccaaaagc | 5160 |
| agggcttcaa ttaagaaatg cctctttgaa aggtgtacct tgggtatcct gtctgagggt | 5220 |
| aactccaggg tgcgccacaa tgtggcctcc gactgtggtt gcttcatgct agtgaaaagc | 5280 |
| gtggctgtga ttaagcataa catggtatgt ggcaactgcg aggacagggc ctctcagatg | 5340 |
| ctgacctgct cggacggcaa ctgtcacctg ctgaagacca ttcacgtagc cagccactct | 5400 |
| cgcaaggcct ggccagtgtt tgagcataac atactgaccc gctgttcctt gcatttgggt | 5460 |
| aacaggaggg gggtgttcct accttaccaa tgcaatttga gtcacactaa gatattgctt | 5520 |
| gagcccgaga gcatgtccaa ggtgaacctg aacgggtgt ttgacatgac catgaagatc | 5580 |
| tggaaggtgc tgaggtacga tgagacccgc accaggtgca gacctgcga gtgtggcggt | 5640 |
| aaacatatta ggaaccagcc tgtgatgctg gatgtgaccg aggagctgag gcccgatcac | 5700 |
| ttggtgctgg cctgcacccg cgctgagttt ggctctagcg atgaagatac agattgaggt | 5760 |
| actgaaatgg aattcctcta gtgatgatga ggctactgct gactctcaac attctactcc | 5820 |
| tccaaaaaag aagagaaagg tagaagaccc caaggacttt ccttcagaat tgctaagttt | 5880 |
| tttgagtcat gctgtgttta gtaatagaac tcttgcttgc tttgctattt acaccacaaa | 5940 |
| ggaaaaagct gcactgctat acaagaaaat tatggaaaaa tattctgtaa cctttataag | 6000 |
| taggcataac agttataatc ataacatact gttttttctt actccacaca ggcatagagt | 6060 |
| gtctgctatt aataactatg ctcaaaaatt gtgtaccttt agctttttaa tttgtaaagg | 6120 |
| ggttaataag gaatatttga tgtatagtgc cttgactaga gatcataatc agccatacca | 6180 |
| catttgtaga ggttttactt gctttaaaaa acctcccaca cctcccctg aacctgaaac | 6240 |
| ataaaatgaa tgcaattgtt gttgttaact tgtttattgc agcttataat ggttacaaat | 6300 |
| aaagcaatag catcacaaat ttcacaaata aagcattttt ttcactgcat tctagttgtg | 6360 |
| gtttgtccaa actcatcaat gtatcttatc atgtctggat ccactagttc tagagcggcc | 6420 |
| gccaccgcgg tggagctcca attcgcccta tagtgagtcg tattacgcgc gctcactggc | 6480 |
| cgtcgtttta acgtcgtg actgggaaaa ccctggcgtt acccaactta atcgccttgc | 6540 |
| agcacatccc cctttcgcca gctggcgtaa tagcgaagag gcccgcaccg atcgcccttc | 6600 |
| ccaacagttg cgcagcctga atggcgaatg ggacgcgccc tgtagcggcg cattaagcgc | 6660 |
| ggcgggtgtg gtggttacgc gcagcgtgac cgctacactt gccagcgccc tagcgcccgc | 6720 |
| tcctttcgct ttcttccctt cctttctcgc cacgttcgcc ggctttcccc gtcaagctct | 6780 |
| aaatcggggg ctccctttag ggttccgatt tagtgcttta cggcacctcg accccaaaaa | 6840 |
| acttgattag ggtgatggtt cacgtagtgg gccatcgccc tgatagacgg ttttcgccc | 6900 |
| tttgacgttg gagtccacgt tctttaatag tggactcttg ttccaaactg gaacaacact | 6960 |
| caaccctatc tcggtctatt cttttgattt ataagggatt ttgccgattt cggcctattg | 7020 |

```
gttaaaaaat gagctgattt aacaaaaatt taacgcgaat tttaacaaaa tattaacgct    7080
tacaatttag                                                          7090
```

PERMANENT AMNIOCYTIC CELL LINE, ITS PRODUCTION AND USE FOR THE PRODUCTION OF GENE TRANSFER VECTORS

CROSS-REFERENCE TO RELATED APPLICATIONS

The application claims the benefit of the filing date of U.S. provisional application serial No. 60/167,439, filed on Nov. 23, 1999, and hereby incorporated by reference.

BACKGROUND OF THE INVENTION

The present invention relates to a permanent amniocytic cell line comprising at least one nucleic acid which brings about expression of the gene products of the adenovirus E1A and E1B regions. The present invention further relates to the production of a permanent amniocytic cell line and to its use for producing gene transfer vectors and/or adenovirus mutants. Further aspects are the use of amniocytes and of the adenoviral gene products of the E1A and E1B regions for producing permanent amniocytic cell lines.

Adenoviruses

Adenoviruses are a relatively homogeneous group of viruses characterized by an icosahedral capsid which consists mainly of the virally encoded hexon, penton and fiber proteins, and of a linear, double-stranded DNA genome with a size of about 36 kilobases (kb). The viral genome contains at the ends the inverted terminal repeat sequences (ITRs) which comprise the viral origin of replication. There is furthermore at the left-hand end of the genome the packaging signal which is necessary for packaging of the viral genome into the virus capsids during an infection cycle. Adenoviruses have been isolated from many species. There are more than 40 different human serotypes based on parameters which discriminate between the various serotypes, such as hemagglutination, tumorigenicity and DNA sequence homology (Wigand et al., in: Adenovirus DNA, Doerfler ed., Martinus Nijoff Publishing, Boston, pp. 408–441, 1986). Adenoviral vectors to date are usually derived from serotypes 2 (Ad2) and 5 (Ad5). Infections by Ad2 and Ad5 are endemic in humans. Ad2 and Ad5 are not oncogenic in humans and have good safety documentation because vaccinations have been performed on military personnel successfully and without complications in the USA (Pierce et al., Am. J. Epidemiol. 87, 237–246, 1968). The biology of adenoviruses is relatively well understood because adenoviruses have played an essential part in molecular biology as experimental tool for elucidating various fundamental biological principles such as DNA replication, transcription, RNA splicing and cellular transformation. Adenoviral particles enter the cell during an infection through receptor-mediated endocytosis in which, according to the current view, interaction of the knob domain of the fiber protein with the coxsackie adenovirus receptor (CAR) mediates adhesion of the virus particle to the cell surface (Bergelson et al., Science 275, 1320–1323, 1997). In a second step there is internalization of the virus particle, for which interaction of the penton base with integrins plays an essential part (Wickham et al., Cell 73, 309–319, 1993). After the particle has entered the cell, the viral genome gets into the cell nucleus as DNA-protein complex. The adenoviral infection cycle is divided into an early and a late phase which are separated by the start of adenoviral replication (Shenk, in: Virology, Fields ed., Lippincott-Raven Publishing, Philadelphia, pp. 2111–2148, 1996). In the early phase there is expression of the early viral functions E1, E2, E3 and E4. The late phase is characterized by transcription of late genes which are responsible for the expression of viral structural proteins and for the production of new viral particles.

E1A is the first viral gene to be expressed by the viral chromosome after the cell nucleus is reached. The E1A gene codes for the 12S and 13S proteins which are formed by alternative splicing of the E1A RNA. The E1A proteins activate the transcription of a number of cellular and viral genes by interacting with transcription factors. The main functions of E1A are a) activation of the other early viral functions E1B, E2, E3 and E4 and b) inducing resting cells to enter the S phase of the cell cycle. Expression of E1A on its own leads to programmed cell death (apoptosis).

E1B is one of the early viral genes activated by E1A. The E1B gene codes for the E1B 55 kD protein and the E1B 19 kD protein, which result through alternative splicing of the E1B RNA. The 55 kD protein modulates the progression of the cell cycle by interacting with the p53 tumor suppressor gene, is involved in preventing the transport of cellular mRNA in the late phase of the infection, and prevents E1A-induced apoptosis of cells. The E1A 19 kD protein is likewise important for preventing E1A-induced apoptosis of cells.

All human adenoviruses are able to transform rodent cells in cell culture. As a rule, coexpression of E1A and E1B is necessry for oncogenic transformation.

The protein IX gene which codes for a structural component of the viral capsid is embedded in the E1B transcription unit.

The E2A and E2B genes code for various proteins which are essential for replication of the viral genome. These comprise the precursor protein of the terminal protein (pTP), the DNA polymerase (Pol) and the single strand-binding protein (SSBP). On replication, pTP binds to the ITRs of the viral genome. There it acts as protein primer for DNA replication, which is initiated by Pol together with cellular factors. Pol, SSBP and the cellular factor NFII, and presumably other factors, are necessary for DNA chain extension.

E4 codes for various proteins. Inter alia, the E4 34 kD protein blocks, together with the E1B 55 kD protein, the accumulation of cellular mRNAs in the cytoplasm, and at the same time it facilitates the transport of viral RNAs from the cell nucleus into the cytoplasm.

After the start of replication of the viral genome there is expression of viral structural proteins which are necessary for establishment of the viral capsid and for complexation of the viral DNA with virally encoded DNA-binding proteins. There is evidently initial formation of an empty capsid, into which the viral genome subsequently enters. A cis element on the viral genome is necessary for this process, the so-called packaging signal which is located at the left-hand end of the viral genome and, in the case of Ad5, extends over a region from base pair 260 to base pair 460 (Hearing et al., J. Virol. 62, 2555–2558, 1987; Graeble and Hearing, J. Virol. 64, 2047–2056, 1990). The packaging signal overlaps with the E1A enhancer which is essential for activity of the E1A promoter. The exact mechanism of the packaging of the viral genome into the virus capsids is not clear but it is probable that interaction of cellular and/or viral proteins with the packaging signal is necessary for this.

Adenovirus Vectors

Adenoviral vectors are particularly important as expression vectors, especially for the purpose of gene therapy. There are several reasons for this: the biology of adenoviruses has been thoroughly investigated. The virus particles are stable and can be produced relatively simply and in high titers. Genetic manipulation of the adenoviral genome is easy. Adenovirus vectors are able efficiently to transduce replicating and nonreplicating cells in vitro and in vi vo.

a) First-generation Adenoviral Vectors

First-generation adenoviral vectors (Gilardi et al., FEBS Letters 267, 60–62, 1990; Stratford-Perricaudet et al., Hum. Gene Ther. 1, 241–256, 1990) are characterized by deletions of the E1A and E1B genes. E1A and E1B have transforming and transactivating properties. In addition, E1A is necessary for activating viral genes and E1B is necessary for the accumulation of viral transcripts. In some vectors in addition E3 is deleted in order to increase the capacity for uptake of foreign DNA. E3 is dispensable for producing adenoviruses in cell culture. The capacity for uptake of foreign DNA is about 8 kb. First-generation adenovirus vectors have to date been produced mainly in 293 cells (see below) which complement the E1A and E1B deficit of the vectors.

b) Second-generation Adenoviral Vectors

Second-generation adenoviral vectors are characterized by deletions of E2 and/or E4 in addition to deletions of E1A and E1B (Engelhardt et al., Proc. Natl. Acad. Sci., USA 91, 6196–6200, 1994; Yang et al., Nature Genet., 7, 362–367, 1994; Gorziglia et al., J. Virol. 70, 4173–4178, 1996; Krougliak and Graham, Hum. Gene Ther. 6, 1575–1586, 1995; Zhou et al., J. Virol. 70, 7030–7038, 1996). In some vectors in addition E3 is deleted in order to increase the capacity for uptake of foreign DNA. Second-generation adenoviral vectors were developed in order to reduce further the transcription of viral genes and the expression of viral proteins and in order thus to diminish further the antiviral immune response. The capacity for uptake of foreign DNA is negligibly increased by comparison with first-generation adenoviral vectors. Second-generation adenovirus vectors are produced in cell lines which, in addition to E1A and E1B, complement the particular deficit (E2 and/or E4).

c) Adenoviral Vectors of Large DNA Capacity

Adenoviral vectors of large DNA capacity are characterized by containing no viral coding DNA sequences (Kochanek et al., Proc. Natl. Acad. Sci. U.S.A. 93, 5731–5736, 1996; Fisher et al., Virology 217, 11–22, 1996; Kumar-Singh and Chamberlain, Hum. Mol. Genet. 5, 913–921, 1996). These vectors only contain the viral ends with inclusion of the ITRs and of the packaging signal. The capacity for uptake of foreign DNA is about 37 kb because by far the major part of the adenoviral genome is deleted. Various systems have been described for producing adenoviral vectors of large DNA capacity (Kochanek et al., supra; Parks et al., Proc. Natl. Acad. Sci. USA 93, 13565–13570, 1996; Hardy et al., J. Virol. 71, 1842–1849, 1997). The advantage of these adenoviral vectors with large DNA capacity compared with first- and second-generation adenoviral vectors is the larger capacity for uptake of foreign DNA and a lower toxicity and immunogenicity (Schiedner et al., Nature Genet. 18, 180–183, 1998; Morral et al., Hum. Gene Ther. 9, 2709–2716, 1998). Currently, adenoviral vectors of large capacity are produced with the aid of an E1A- and E1B-deleted helper virus which provides the viral functions necessary for a productive infection cycle in trans. To date, adenoviral vectors of large DNA capacity have been produced in 293 cells or in cell lines derived from 293 cells. In one of the production methods (Parks et al., supra; Hardy et al., supra), adenoviral vectors are produced in modified 293 cells which, in addition to E1A and E1B, express the Cre recombinase of bacteriophage P1. In this system, the packaging signal of the helper virus is flanked by loxP recognition sequences of bacteriophage P1. On infection of Cre-expressing 293 cells with helper virus and the adenoviral vector of large DNA capacity, the packaging signal of the helper virus is excised. For this reason there is packaging mainly of the vector containing a normal packaging signal but not of the helper virus.

d) Deleted Adenoviral Vectors

These vectors have been described as first-generation vectors which have the loxp recognition sequences of bacteriophage P1 positioned in the viral genome in such a way that, on infection of Cre-expressing 293 cells, most of the viral coding sequences or all the viral coding sequences are deleted by recombination between the loxP recognition sequences. The size of the genome of these vectors is about 9 kb. The capacity for uptake of foreign DNA is likewise about 9 kb (Lieber et al., J. Virol. 70, 8944–8960, 1996).

Adeno-associated Virus (AAV)

AAV belongs to the family of parvoviruses, genus dependovirus, and has two different life forms, occurring either as lytic virus or as provirus. For a lytic infection to take place the virus requires coinfection with a helper virus (adenovirus, vacciniavirus, herpes simplex virus). In the absence of a helper virus, AAV is unable to replicate, integrates into the genome and exists there as inactive provirus. When cells harboring AAV as integrated provirus are infected, for example with adenovirus, the provirus is able to enter a lytic infection cycle again (Samulski, Curr. Opin. Genet. Dev. 3, 74–80, 1993).

AAV capsids contain a single-stranded, linear DNA genome with either positive or negative polarity. Several AAV serotypes exist. The serotype which has been investigated most is AAV-2. The genome of AAV-2 consists of 4680 nucleotides. The genome contains at the ends inverted terminal repeat sequences (ITRs) having a length of 145 base pairs. The first 125 base pairs form a T-shaped hairpin structure consisting of two internal palindromes.

The AAV genome codes for nonstructural replication (Rep) proteins and for structural capsid (Cap) proteins. The various replication proteins (Rep78, Rep68, Rep52, Rep40) are generated by using different promoters (p5 and p19) and by alternative splicing. The various capsid proteins (VP1, VP2, VP3) are generated by alternative splicing using the p40 promoter.

AAV Vectors

AAV vectors contain only the ITRs of AAV and some adjacent, noncoding AAV sequences. For this reason, the capacity for uptake of foreign DNA is about 4.5 kb. Various systems have been described for producing recombinant AAV vectors (Skulimowski and Samulski, in: Methods in Molecular Genetics, Vol. 7, Adoph ed., Academic Press, pp. 3–12). The components necessary for replication, expression and packaging of the recombinant vector are provided in these systems. Specifically, these are expression cassettes which code for the Rep and Cap proteins of AAV, and the adenoviral helper functions. The adenoviral helper functions necessary for AAV production are, specifically, E1A, E1B, E2, E4 and VA. The E1A and E1B functions are provided in the 293 cells which have been used for production to date. In the production processes described to date, the E2, E4 and VA functions are currently usually provided either by coinfection with adenovirus or by cotransfection with E2-, E4- and VA-expressing plasmids (Samulski et al., J. Virol. 63, 3822–3828, 1989; Allen et al., J. Virol. 71, 6816–6822, 1997; Tamayose et al., Hum. Gene Ther. 7, 507–513, 1996; Flotte et al., Gene Ther. 2, 29–37, 1995; Conway et al., J. Virol. 71, 8780–8789, 1997; Chiorini et al., Hum. Gene Ther. 6, 1531–1541, 1995; Ferrari et al., J. Virol. 70, 3227–3234, 1996; Salvetti et al., Hum. Gene Ther. 9, 695–706, 1998; Xiao et al., J. Virol. 72, 2224–2232, 1998, Grimm et al., Hum. Gene Ther. 9, 2745–2760, 1998; Zhang et al., Hum. Gene Ther. 10, 2527–2537, 1999). Alternatively, strategies have been developed in which adenovirus/AAV or herpes simplex virus/AAV hybrid vectors have been used to produce AAV vectors (Conway et al., supra; Johnston et al., Hum. Gene Ther. 8, 359–370, 1997, Thrasher et al., Gene Ther. 2, 481–485, 1995; Fisher et al., Hum. Gene Ther. 7, 2079–2087, 1996; Johnston et al., Hum. Gene Ther. 8, 359–370, 1997). It is common to all these processes that E1A- and E1B-expressing 293 cells are currently used for production.

Producer Cell Lines

For safety reasons, adenoviral vectors intended for use in humans usually have deletions of the E1A and E1B genes. Production takes place in complementing cell lines which provide the E1 functions in trans. Most adenoviral vectors to date have been produced in the 293 cell line. In recent years, further cell lines which can be used to produce E1-deleted adenoviral vectors have been produced.

a) HEK 293 Cells

HEK 293 cells were for a long time the only cells which could be used to produce E1-deleted adenoviral vectors. HEK 293 cells were produced in 1977 by transfection of sheared adenoviral DNA into human embryonic kidney cells (HEK cells). In a total of eight transfection experiments each with an average of 20 HEK cultures it was possible to obtain only a single immortalized cell clone (Graham et al., J. Gen. Virol. 36, 59–74, 1977). The cell line (HEK 293 cells) established from this cell clone contains the complete left-hand 11% of the adenoviral genome (base pair 1 to 4344 of the Ad5 genome), including the E1A and E1B genes and the left-hand ITR and the adenoviral packaging signal (Louis et al., Virology 233, 423–429, 1997). A considerable problem for the production of adenoviral vectors is the sequence homology between E1-deleted adenoviral vectors and the portion of adenoviral DNA integrated into 293 cells. Homologous recombination between the vector genome and the adenoviral DNA integrated into 293 cells is responsible for the generation of replication-competent adenoviruses (RCA) (Lochmüller et al., Hum. Gene Ther. 5, 1485–1491, 1994; Hehir et al., J. Virol. 70, 8459–8467, 1996). HEK 293 cells are for this reason unsuitable for producing adenoviral vectors of pharmaceutical quality because production units are often contaminated with unacceptable amounts of RCA. RCA is unacceptable in products produced for clinical use because replication-competent adenoviruses have a distinctly higher toxicity than replication-defective adenoviruses, are capable of uncontrolled replication in human tissues, and are moreover able to complement replication-defective adenoviruses (Lochmüller et al., supra; Imler et al., Hum. Gene Ther. 6, 711–721, 1995; Hehir et al., supra).

b) Human Embryonic Retinal Cells (HER Cells) and Established Cell Lines

Although rodent cells can easily be transformed with adenoviral E1 functions, primary human cells have proved to be relatively resistant to transformation with E1A and E1B. As mentioned above, Graham and coworkers were able to isolate only a single cell clone from HEK cells which had been transfected with sheared Ad5 DNA. Gallimore and coworkers attempted for a long time unsuccessfully to transform primary HEK cells with E1 functions of Ad12 (Gallimore et al., Anticancer Res., 6, 499–508, 1986). These experiments were carried out unsuccessfully over a period of three years with more than 1 mg of the EcoRI cDNA fragment of Ad12 containing the E1A and E1B genes. After many attempts it was possible, despite a large number of experiments carried out, to isolate only four Ad12-E1 HEK cell lines (Whittaker et al., Mol. Cell. Biol., 4, 110–116, 1984). Likewise, Gallimore and coworkers attempted unsuccessfully to transform other primary human cells with E1 functions, including keratinocytes, skin fibroblasts, hepatocytes and urothelial cells (Gallimore et al., Anticancer Res., 6, 499–508, 1986). The only human cell type which it has been possible to date to transform reproducibly with adenoviral E1 functions comprises human embryonic retinal cells (HER cells). HER cells are a mixture of cells derived from the white neural retina. To obtain these cells it is necessary to remove the eye from the orbital cavity of a human fetus, normally between weeks 16 and 20 of gestation. The eye is opened with a horizontal incision and the white neural retina can be removed with forceps and placed in cell culture.

Based on earlier observations that a) Ad12-induced tumors are primarily derived from primitive neural epithelium (Mukai et al., Prog. Neuropathol. 3, 89–128, 1976) and that b) Ad12 induces retinal tumors in rats and baboons after intraocular inoculation (Mukai et al., supra; Mukai et al., Science 210, 1023–1025, 1980), Byrd and coworkers found that human embryonic retinoblasts (HER cells) can be transformed with the E1 genes of Ad12 (Byrd et al., Nature 298, 69–71, 1982). Although the efficiency of transformation of HER cells was less than that of primary rat cells, the efficiency of transformation was more than 100 times higher than that of HEK cells. The investigations were initiated in order to produce complementing cell lines which could be used to isolated Ad12 E1 mutants.

In further investigations by this research group (Gallimore et al., Cancer Cells 4, 339–348, 1986) it was shown that HER cells can be transformed efficiently with plasmid DNA which expresses the E1A and E1B genes of Ad5. The efficiency of transformation and the establishment of E1A- and E1B-expressing cell lines was about 20 times higher with the E1 genes of Ad5 than with E1 genes of Ad12.

Based on these data, Fallaux and coworkers (Fallaux et al., Hum. Gene Ther. 7, 215–222, 1996; Fallaux et al., Hum. Gene Ther. 9, 1909–1917, 1998) established E1A- and E1B-expressing cell lines by transforming HER cells with plasmids which expressed the E1A and E1B genes of Ad5. The cell line 911 was produced by transformation with a plasmid which contains the E1A and E1B genes of Ad5 (nucleotides 79–5789 of the Ad5 genome) and expresses E1A under the control of the natural E1A promoter (Fallaux et al., supra; Patent Application WO97/00326). It was possible to establish further E1A- and E1B-expressing HER cell lines by transfecting a plasmid which contains nucleotides 459–3510 of the Ad5 genome, in which the E1A gene is under the control of the human phosphoglycerate kinase (PGK) promoter, and in which the natural E1B polyadenylation signal is replaced by the poly(A) sequence of the heptatitis B virus (HBV) surface antigen (Fallaux et al., supra; Patent Application WO97/00326). These HER cell lines have been referred to as PER cell lines. The advantage of these newer PER cell lines compared with 293 cells or the 911 cell line is the lack of sequence homology between the DNA of first-generation adenoviral vectors and the integrated Ad5 DNA. For this reason there is a marked reduction in the possibility of the generation of RCA. These E1A- and E1B-transformed HER cell lines (911 cells and PER cells) were able to complement the E1 deficit of first-generation adenoviral vectors and thus be used to produce these vectors.

In a similar way, a cell line which was established by transforming HER cells with the plasmid pTG6559 is mentioned in a publication by Imler and coworkers (Imler et al., supra; see also WO 94/28152). The plasmid pTG6559 contains the coding sequences of the E1A and E1B genes and of the protein IX gene (nucleotides 505–4034 of the Ad5 genome), with the E1A gene being under the control of the mouse phosphoglycerate kinase (PGK) promoter, and the joint polyadenylation signal of the E1B and protein IX genes having been replaced by the polyadenylation signal of the rabbit β-globin gene.

In contrast to the described attempts to establish primary human cells by transformation with the E1A and E1B genes of Ad5, attempts have been made in a few cases to express E1A and E1B of various serotypes stably in previously established cell lines (Grodzicker et al., Cell, 21, 453–463, 1980; Babiss et al., J. Virol. 46, 454–465, 1983; Shiroki et al., J. Virol. 45, 1074–1082, 1983; Imler et al., supra; see also WO 94/28152). The disadvantages of these cell lines are the need for coexpression of a selection marker and the frequently deficient stability of E1A and E1B expression. Since these cell lines are immortalized cell lines from the outset, expression of E1A and E1B is not necessary for survival of the cell lines, so that natural selection by E1A and E1B is unnecessary in this case and in contrast to the use of primary cells.

In the past, the production of cell lines for producing adenoviral vectors or for producing AAV vectors was associated with particular difficulties. Human embryonic kidney cells (HEK cells) can be obtained from the kidney of human fetuses. This is done by removing a kidney from a fetus and placing kidney cells in the cell culture. Transfection of HEK cells with sheared Ad5 DNA and integration of the left-hand end of the Ad5 DNA, and expression of the E1A and E1B genes resulted in transformation of the cells in a single published case. It was possible to establish a single cell line (293 cells) in this way (Graham et al., supra; see above "Producer cell lines", section a). 293 cells are used to produce adenoviral vectors and to produce AAV vectors.

Human embryonic retinal cells (HER cells) can be obtained from the eyeball of human fetuses. This is done by removing an eye from the fetus and placing cells from the retina in culture. It was possible by transfecting HER cells with the adenoviral E1A and E1B genes to transform HER cells (see above "Producer cell lines", section b). Cells transformed with E1A and E1B can be used to produce adenoviral vectors.

It is necessary in both cases to remove an organ from human fetuses, which are derived either from a spontaneous or therapeutic abortion or from a termination of pregnancy on social grounds, and to establish a cell culture from this organ. After establishment of a primary culture, these cells can then be transformed by transfection with the adenoviral E1A and E1B genes. Cell lines established in this way and expressing E1A and E1B can then be used to produce adenoviral vectors or AAV vectors.

It is evident that it is complicated to obtain primary cells from organs from fetuses. Since a primary culture can be established only from fresh tissue, special logistic efforts are needed to obtain suitable tissue. In addition, the use of fetal tissue derived either from a spontaneous abortion, a therapeutic abortion or from a termination of pregnancy on social grounds makes special ethical considerations and care necessary for establishment of a primary culture. Although the inventors' laboratory is situated in a gynecology clinic where terminations of pregnancy are frequently performed, it was not possible to obtain suitable tissue over a period of more than one year. Removal of fetal tissue after abortion requires a declaration of consent by the pregnant woman after receiving appropriate information. It was frequently impossible to obtain the consent of the pregnant woman for the organ-removal intervention after she had received detailed information about the project, i.e. the removal of an eye from the fetus for scientific medical investigations.

The use of a permanent amniocytic cell line for producing gene transfer vectors has not previously been described. There have merely been a report of human amniocytes which have been transformed with the simian virus (SV40) and/or the Kirsten sarcoma virus (Sack, In Vitro 17 pp. 1–19, 1981; Walen, et al., In Vitro Cell Dev. Biol. 22, 57–65, 1986). Infection with SV40 alone conferred an extended lifetime (called immortalization), whereas infection with the Kirsten sarcoma virus alone did not extend the lifespan. Infection with both viruses finally led to a malignant tumor cell (Walen and Arnstein, supra). It should be noted in this connection that SV40-transformed amniocytic cell lines are unsuitable for producing gene transfer vectors because these cells themselves produce SV40, which is known to be an oncogenic virus (Graffney et al., Cancer Res. 30, 871–879, 1970). The transformability of human cells with SV40 moreover provides no information about the transformability with the E1 functions of adenovirus and the use thereof for the production of gene transfer vectors. For example, keratinocytes can be transformed with SV40 (see Sack, supra), but keratinocytes evidently cannot, just like skin fibroblasts and hepatocytes, be transformed with Ad12 (Gallimore et al., 1986, supra). In terms of the production of viral vectors, especially adenoviral vectors, in immortalized cells, moreover, it is not just the immortalizability with the particular immortalization functions which is important; so too are good infectability and a good productive course of infection. These properties cannot be predicted; the question of whether a particular cell type can be used for producing gene transfer vectors must be determined anew for each cell type.

An object of the present invention was herefore to provide a novel process for the efficient, simple and easily reproducible production of an amniocytic cell line, and the use thereof inter alia for producing adenoviral vectors, AAV vectors and retroviral or lentiviral vectors.

SUMMARY OF THE INVENTION

It has been found, entirely surprisingly, that transfection of cells of the amniotic fluid (amniocytes), which are routinely obtained by amniotic fluid biopsy (amniocentesis) for diagnostic reasons during prenatal diagnosis, with the adenoviral E1A and E1B genes led to a large number of permanent cell lines which expressed the E1A and E1B genes in a functionally active manner and which are suitable for producing gene transfer vectors.

One aspect of the present invention is therefore a permanent amniocytic cell line comprising at least one nucleic acid which brings about expression of the gene products of the adenovirus E1A and E1B regions. A "permanent cell line" means according to the present invention that the corresponding cells have been genetically modified in some way so that they are able to continue growing permanently in cell culture. By contrast, "primary cells" mean cells which have been obtained by removal from an organism and subculturing and which have only a limited lifetime. A permanent amniocytic cell line for the purpose of the present invention can be obtained by the process proposed herein, which comprises the transfection of primary amniocytes with the E1 functions of adenovirus. The at least one nucleic acid which brings about expression of the adenovirus E1 gene products can be any suitable nucleic acid or nucleic acids which lead to stable expression of these gene products. It/they can be integrated into the genome of the cell, i.e.

chromosomally, or be present outside the chromosome, for example as episomally replicating plasmid or minichromosome. Expression of the various gene products can moreover be brought about by one and the same nucleic acid molecule or, for example, different nucleic acid molecules. "Expression" means in the state of the art the process of production of a gene product which is a specific protein which brings about a specific trait or a specific property, or of RNA forms which are not translated into proteins (for example antisense RNAs, tRNAs). Suitable possibilities for achieving the desired expression will be evident to the skilled worker in the light of the present description, in particular of the proposed process too. The novel amniocytic cell line is suitable not only for use for producing gene transfer vectors in general but also, in particular, for producing first-generation adenoviral vectors characterized by deletions of the E1A and E1B genes, which are complemented by the cell line.

The at least one nucleic acid also preferably brings about expression of the gene products of the adenovirus E2A, E2B and/or E4 regions and/or of Cre recombinase. This makes the cell line particularly suitable for producing second-generation adenoviral vectors which are characterized by deletions of E2 and/or E4 genes in addition to the deletions of the E1A and E1B genes. Expression of the Cre recombinase of bacteriophage P1 is particularly advantageous in the production of adenoviral vectors of large capacity with the aid of an E1A- and E1B-deleted helper virus (see also Parks et al., supra; Hardy et al., supra). Expression of the gene products of the E1A region is advantageously under the control of a constitutive promoter, preferably the phosphoglycerate kinase (PGK) promoter. It is advantageous for expression of the gene products of the E1B region if it is under the control of an adenoviral promoter, preferably the adenoviral E1B promoter. A possible alternative to this is to employ, for example, a cytomegalovirus (CMV) promoter. All the adenoviral gene products are preferably derived from an adenovirus of the same subgenus, for example of human adenovirus type 5 (Ad5). The permanent amniocytic cell line is normally a human cell line, because this is particularly suitable for producing gene transfer vectors derived from human viruses, such as, for example, a human adenovirus or a human AAV.

A possible alternative to this is a cell line from primates or other mammals such as, for example, bovines, which is particularly suitable for producing gene transfer vectors derived from viruses occurring and endemic in particular species. For example, permanent amniocytic cell lines obtained by transformation of amniocytes with the E1A and E1B genes of a bovine adenovirus are suitable for producing vectors derived from a bovine adenovirus.

Another aspect of the present invention is a process for producing a permanent amniocytic cell line, in particular an amniocytic cell line as defined above, which comprises the transfection of amniocytes with at least one nucleic acid which brings about expression of the adenoviral gene products of the E1A region and E1B region. The resulting cell clones can then be isolated further where appropriate and, if required, be cloned to obtain single cell lines. The term "transfection" means herein any process suitable for introducing said nucleic acid(s) into the cells. Examples which may be mentioned are electroporation, liposomal systems of any type and combinations of these processes. The term "amniocytes" means herein in the wider sense all cells which are present in the amniotic fluid and can be obtained by amniotic fluid biopsy. They are derived either from the amnion or from fetal tissue which is in contact with the amniotic fluid. Three main classes of amniocytes have been described and are distinguished on the basis of morphological criteria: fibroblast-like cells (F cells), epitheloid cells (E cells) and amniotic fluid cells (AF cells) (Hohn et al., Pediat. Res. 8, 746–754, 1974). AF cells are the predominant cell type. In the narrow sense, therefore, "amniocytes" mean herein amniocytes of the AF type. Primary amniocytes are preferably used. Cells referred to as "primary" cells are those which can be obtained by removal from an organism and subculturing and have only a limited lifetime, whereas so-called "permanent" cell lines are able to continue to grow unrestrictedly. It is particularly preferred in this connection to use human primary amniocytes which lead to the production of human cell lines (see above). However, it is also possible to use primary amniocytes from primates and other mammalian species such as from bovines. It will also be evident to the skilled worker in the light of the present description that it is possible to use analogously cells which can be obtained from the amniotic membranes, for example by trypsinization, or by a chorionic villus biopsy, for producing corresponding permanent cell lines.

The at least one nucleic acid which brings about expression of the adenoviral E1 gene products can be genomic DNA, cDNA, synthetic DNA, RNA and mRNA. The nucleic acid is preferably used in the form of a DNA expression vector. Examples thereof are integrative vectors, bacterial plasmids, episomally replicated plasmids or minichromosomes. Preference is given to expression plasmids whose integration into the genome of the recipient cell is brought about by transfection. The term "at least one nucleic acid" expresses the fact that the elements which bring about the expression may be present either on one and the same nucleic acid or on different nucleic acids. For example, separate nucleic acids may be provided for expression of the gene products of the E1A, E1B, E2A, E2B and/or E4 regions and/or of Cre recombinase. It is also conceivable that the amniocytes to be transfected already express one of these gene products so that only the expression of the other gene product(s) needs to be brought about, or that the expression of one or more of these gene products is switched on merely by introducing suitable regulatory elements. Suitable techniques and processes for the production and, where appropriate, mutagenesis of nucleic acids and for gene expression and protein analysis are available to the skilled worker (see, for example, Sambrook, J. et al., Molecular Cloning: A Laboratory Manual, Cold Spring Harbor Laboratory Press (1989); Glover, D. M., DNA cloning: A practical approach, vol. II: Expression Systems, IRL Press (1995); Ausubel et al., Short protocols in molecular biology, John Wiley & Sons (1999); Rees, A. R. et al., Protein engineering: A practical approach, IRL press (1993)). It is preferred for the gene product or gene products of the E1A region to be expressed under the control of a constitutive promoter, in particular the phosphoglycerate kinase (PGK) promoter, and for the gene products of the E1B region to be expressed under the control of an adenoviral promoter, in particular the adenoviral E1B promoter. In place of the adenoviral promoter it is also possible to use, for example, a cytomegalovirus (CMV) promoter.

In a particular embodiment, transfection of the amniocytes and/or of the resulting cell line additionally brings about expression of the resulting gene products of the adenovirus E2A and/or E2B and/or E4 regions and/or of Cre recombinase. All the possibilities discussed previously or otherwise disclosed in the prior art are available to the skilled worker in this connection. Concerning the individual genes, reference is made in addition to the following information: E2A: Genbank Acc. #M73260; Kruiyer et al., Nucl. Acids Res. 9, 4439–4457, 1981; Kruiyer et al., Nucl. Acids Res. 10, 4493–4500, 1982. E2B: Genbank Acc. #M73260; Dekker et al., Gene 27, 115–120, 1984; Shu et al., Virology 165, 348–356, 1988. E3: Genbank Acc. #M73620; Cladaras et al., Virology 140, 28–43, 1985. E4: Genbank Acc. #M73620 and D12587; Virtanen et al., J. Virol. 51, 822–831, 1984; Dix et al., J. Gen. Virol. 73, 2975–2976, 1992. The reading frames are in some cases known only for Ad2 and can then usually be assigned by comparison of sequences in the case of, for example, Ad5. Cre recombinase: Genbank Acc. #X03453; Sternberg et al., J. Mol. Biol. 187, 197–212, 1986.

The adenoviral gene products are preferably all derived from a particular adenoviral serotype, in particular from human adenovirus type 5 (Ad5). The particular adenoviral serotype which is the origin of the E1A and E1B genes used for transforming amniocytes is not critical for this invention. Examples of adenoviral serotypes which can be used in the present invention are known in the prior art and include more than 40 human serotypes, for example Ad12 (subgenus A), Ad3 and Ad7 (subgenus B), Ad2 and Ad5 (subgenus C), Ad8 (subgenus D), Ad4 (subgenus E), Ad40 (subgenus F) (Wigand et al., in: Adenovirus DNA, Doerfler, ed., Martinus Nijhoff Publishing, Boston, pp. 408–441, 1986). In a preferred embodiment of this invention, adenoviral vectors derived from subgenus C are produced by transforming amniocytes with E1A and E1B genes which are derived from an adenovirus of the same subgenus. For example, adenoviral vectors of serotype 2 or 5 are produced by transforming amniocytes with the E1A and E1B genes of serotype 2 or 5. Adenoviral vectors based on Ad12 are produced by transforming amniocytes with the E1A and E1B genes of Ad12 etc. To produce non-human adenoviral vectors, including of the well-known adenoviruses derived from cattle, sheep, pigs and other mammals, amniocytic cell lines are produced by transforming amniocytes of the particular species. This is usually necessary because adenoviral functions usually cannot be complemented efficiently beyond species boundaries.

In a particular embodiment of the invention, amniocytes obtained for diagnostic reasons within the scope of prenatal diagnosis by amniotic fluid biopsy and no longer used for diagnostic purposes were transfected with an expression plasmid which expressed the E1A and E1B genes of Ad5. This construct was, designed so that the E1A gene was under the control of the mouse phosphoglycerate kinase promoter, and the E1B gene was under the control of the natural adenoviral E1B promoter. The natural E1B splice acceptor site and the E1B polyadenylation sequence were replaced by the corresponding sequences of the SV40 virus. A few weeks after transfection with the plasmid DNA, a large number of cell clones was observed, and these were isolated, cloned, established as immortalized cell lines and analyzed. All the analyzed cell clones expressed the E1A and E1B proteins. It was shown, by infection with an E1-deleted, β-gal-expressing adenoviral vector and subsequent staining, that all these cells could be infected. Infection experiments with E1-deleted first-generation adenoviral vectors revealed that the cell lines are suitable for producing adenoviral vectors. In these experiments, the cell lines were initially infected with a β-gal-expressing first-generation adenoviral vector. After 48–72 hours, when the cells showed a cytopathic effect (CPE), the cells were harvested and the adenoviral vector was freed of cells by freezing and thawing three times. Part of the cell lysate was used to infect 293 cells, and β-gal expression was detected histochemically about 24 hours after the gene transfer. It was possible to calculate directly from the number of β-gal-positive cells the yield of the vector by production in the individual cell lines. Amniocytic cell lines can be obtained in this way without difficulty and reproducibly and are very suitable for producing gene transfer vectors. Some of the isolated cell lines allowed adenoviral vectors to be produced just as well as or better than 293 cells. As was to be expected, the cell lines showed differences in the production of recombinant adenovirus vector (see FIG. 4). The cell lines N52.E6 and N52.F4 were distinguished by a rapid growth and particularly good production of adenoviral vectors, beneficial properties for the use of these cell lines for producing gene transfer vectors.

The design of the E1A- and E1B-expressing expression plasmid used for transforming the amniocytes precludes the generation of replication-competent adenoviruses (RCA) by homologous recombination of an adenoviral vector or of an adenoviral helper virus with the DNA integrated into the transformed amniocytes, in contrast to 293 cells. As an alternative to this, the individual E1 functions can be introduced on various expression plasmids into the cells to be transfected. It is, of course, also possible, as for the 293 cell line, to carry out a transformation of amniocytes and to test the batches generated in the production of gene transfer vectors for the RCA content, for example using a PCR or infection assay. The RCA-containing batches can then be discarded where appropriate.

Thus a further aspect of the present invention relates to a permanent amniocytic cell line which can be obtained by the process proposed herein. In a specific embodiment, the invention relates to the permanent amniocytic cell line N52.E6 which was deposited on Oct. 26, 1999 at the Deutsche Sammlung von Mikroorganismen und Zellkulturen GmbH (DSMZ) in accordance with the Budapest treaty and has received the accession number DSM ACC2416.

In a further aspect, the present invention relates to the use of amniocytes for producing adenovirus-transformed permanent amniocytic cell lines. The term "adenovirus-transformed" means herein transformation by one or more transforming adenovirus genes. "Transformation" refers in this connection to conversion of a eukaryotic cell which is subject to growth control into a so-called permanent cell line which grows unrestrictedly. A further aspect is the use of the adenoviral gene products of the E1A and E1B regions for producing permanent amniocytic cell lines.

The present invention further comprises the use of a permanent amniocytic cell line for producing gene transfer vectors. "Gene transfer vectors" mean herein generally all vectors with which one or more therapeutic genes can be transferred or introduced into the desired target cells and, in particular, viral vectors having this property. In addition, the permanent amniocytic cell lines can be used to produce adenovirus mutants. "Adenovirus mutants" mean adenoviruses which have at least one mutation in the E1A and/or E1B genes. In a preferred embodiment, they do not, however, in contrast to adenoviral gene transfer vectors, harbor any therapeutic genes. A typical example thereof comprises adenovirus mutants in which the E1B 55 kD protein is not expressed (for example the adenovirus mutant dl1520 (Barker et al., Virology 156, 107–121, 1987)). Adenovirus mutants in which the E1B 55 kD protein is not expressed are of great interest for the therapy of oncoses because the virus mutant replicates exclusively in tumor cells and not or to a negligible extent in primary normal cells (Bischoff et al., Science 274, 373–376, 1996; Kirn et al., Nature Med. 4, 1341–1342, 1998).

A preferred embodiment is the use of a permanent amniocytic cell line for producing adenovirus vectors, AAV (adeno-associated virus) vectors, retrovirus vectors, lentivirus vectors, chimeric adenovirus-AAV vectors, chimeric adenovirus-retrovirus vectors and/or chimeric adenovirus-lentivirus vectors. A use for producing herpes vectors is also possible.

AAV vectors normally comprise only the ITRs of AAV and some adjacent, noncoding AAV sequences. Their capacity for uptake of foreign DNA is about 4.5 kb. As described above, various systems exist for producing recombinant AAV vectors. It is common to all these systems that the components necessary for replication, expression and packaging of the recombinant vector are provided. Specifically, these comprise expression cassettes which code for the AAV rep and cap proteins, and the adenoviral helper functions. The adenoviral helper functions necessary for AAV production are the E1A, E1B, E2, E4 and VA genes. The E1A and E1B functions are provided in the E1A- and E1B-expressing amniocytic cell lines and can therefore be used to produce AAV vectors. The E2, E4 and VA functions can be provided by coinfection with adenovirus or by cotransfection with E2-, E4- and VA-expressing plasmids or by using adenovirus/AAV or herpes simplex virus/AAV hybrid vectors (Samulski et al., supra; Allen et al., supra; Tamayose et al., supra; Flotte et al., supra; Conway et al., supra; Chiorini et al., supra; Ferrari et al., supra; Salvetti et al., supra; Xiao et al., supra; Grimm et al., supra; Zhang et al., supra).

Retrovirus vectors, that is to say vectors derived from retroviruses, are likewise of great importance as vehicles for transfection within the scope of gene therapeutic procedures, for example for gene therapy in the central nervous system (Suhr et al., Arch. Neurol. 56, 287–292, 1999). Retroviral vectors can be produced in stable vector-producing cell lines or by transient transfection. The individual components used to produce retroviral vectors normally include one or more plasmids which express the structural proteins and the replication and integration proteins, as well as a plasmid which comprises the vector itself (Miller, in:. Retroviruses, Coffin, Hughes, Varmus ed., Cold Spring Harbor Laboratory Press, 1997, pp. 437–473). If those plasmids which contain an origin of replication, such as, for example, the SV40 origin of replication, are used, the amniocytic cell lines are modified so that proteins which promote replication of the plasmid are stably expressed. For example, in the case of plasmids which contain the SV40 origin of replication, an amniocytic cell line which expresses the T antigen of SV40 is used.

Lentivirus vectors are vectors derived from lentiviruses (Naldini et al., Science 272, 263–267, 1996; Dull et al., J. Virol. 72, 8463–8471, 1998). Lentiviral vectors can be produced in stable vector-producing cell lines or by transient transfection.

"Chimeric vectors" mean vectors which are the product of a fusion of nucleic acids from two or more different viral vectors. Permanent amniocytic cell lines can be used according to the present description for producing chimeric vectors. In this system, for example, an adenovirus vector, preferably an adenovirus vector of large capacity, harbors a DNA fragment which has the sequence information for an integrating virus which is derived, for example, from a retrovirus or from AAV. After transcription of a target cell, the integrating virus harboring a therapeutic gene is released from the adenoviral background (for example in the case of a retroviral insert by producing infectious retroviral particles which transduce neighboring cells and integrate stably as DNA). Examples of chimeric vectors produced in 293 cells have been described in the past, for example as chimeric adenovirus-retrovirus vectors (Feng et al., Nature Biotech. 15, 866–870, 1997) and as chimeric adenovirus-AAV vectors (Recchia et al., Proc. Natl. Acad. Sci. USA 96, 2615–2620, 1999). Production in E1A and E1B-expressing amniocytic cell lines is to be preferred because, in contrast to 293 cells, replication-competent vectors cannot be generated by homologous recombination.

Adenovirus vectors, that is to say vectors derived from adenoviruses, are of great importance in particular as vehicles for transfection within the scope of gene therapeutic procedures. The adenovirus vectors may be first-generation adenovirus vectors, second-generation adenovirus vectors, adenovirus vectors of large DNA capacity and/or deleted adenovirus vectors, which are produced with the aid of a permanent amniocytic cell line.

a) Production of First-generation Adenoviral Vectors

First-generation adenoviral vectors are usually characterized by deletions of the E1A and E1B genes. Some first-generation adenoviral vectors comprise, in addition to the deletion of the E1A and E1B genes, also deletions of the E3 region. E3 functions are dispensable for the growth of adenoviral vectors in cell culture.

First-generation adenoviral vectors can be produced in E1A- and E1B-expressing amniocytic cell lines. This is done by infecting the E1A- and E1B-expressing cells preferably with 3–5 infectious units per cell (3–5 MOI). After about 36 to 72 hours, the cells show a cytopathic effect. The cells are harvested by standard protocols. Adenoviral vector can be purified from them by CsCl density gradient centrifugation or by chromatographic processes.

b) Production of Second-generation Adenoviral Vectors

Second-generation adenoviral vectors are characterized by deletions of E1A and E1B genes. Some second-generation adenoviral vectors also comprise a deletion of the E3 region. In addition to the deletion of the E1A and E1B genes, second-generation adenoviral vectors are characterized by inactivation and preferably deletion of at least one other essential adenoviral gene, for example an E2A gene, an E2B gene and/or a E4 gene, or, for example, by deletions of E2 functions in combination with deletions of E4 functions.

To produce second-generation adenoviral vectors, the functions which the vector itself does not express, due to inactivation and/or deletion, must be provided by the amniocytic cell line. For this purpose, it is possible for amniocytic cell lines which stably express E1A and E1B to be stably modified by transfection of expression cassettes which express the gene products coding for one or more other adenoviral functions. For example, to produce a second-generation adenoviral vector which has, in addition to the deletion of the E1A and E1B genes, also a deletion of an E2A, E2B and/or E4 gene, the appropriate gene or genes is (are) introduced by transfection together with a selection marker into the E1A- and E1B-expressing amniocytic cell line. Cell clones which, in addition to the expression of E1A and E1B functions, also express E2A, E2B and/or E4 functions can then be used to produce the particular second-generation vector. The E2 and/or E4 genes are usually under the transcriptional control of a heterologous promoter, which either is constitutively active or can be regulated.

c) Production of Adenoviral Vectors of Large DNA Capacity

Adenoviral vectors of large DNA capacity are characterized by deletion of most or all of the viral coding sequences. These vectors preferably comprise only the viral ITRs and the viral packaging signal. The adenoviral functions are provided by a helper virus in trans. Various systems for producing adenoviral vectors of large DNA capacity have been described. It is common to all the systems described to date and using a helper virus that the helper virus corresponds to a replication-deficient, E1A- and E1B-deleted adenovirus. The helper virus comprises either a complete packaging signal (Mitani et al., Proc. Natl. Acad. Sci. USA 92, 3854–3858, 1995; Fisher et al., Virology 217, 11–22, 1996; Kumar-Singh and Chamberlain, Hum. Mol. Genet. 5, 913–921, 1996) or a mutated packaging signal (Kochanek et al., Proc. Natl. Acad. Sci. U.S.A. 93, 5731–5736, 1996). In the latter case, the vector is preferably packaged in viral capsids because the helper virus contains an attenuated packaging signal and therefore is packaged less efficiently. Alternatively, the packaging signal of the helper virus can be excised after the infection of the producer cell line by using a recombinase (Parks et al., Proc. Natl. Acad. Sci. USA 93, 13565–13570, 1996; Hardy et al., J. Virol. 71, 1842–1849, 1997). For example, the packaging signal of the helper virus can be flanked by loxP recognition sequences of bacteriophage P1. Expression of the Cre recombinase of bacteriophage P1 results in excision of the packaging signal of the helper virus. However, because of the absence of the packaging signal, no packaging of the helper virus into capsids takes place. The Cre recombinase gene of bacteriophage P1 is introduced by transfection together with a selection marker into the E1A- and E1B-expressing amniocytic cell line. Cell clones which, in addition to expression of E1A and E1B functions, also express the Cre function of bacteriophage P1 can then be used to produce the particular vector of large DNA capacity.

d) Production of "Deleted" Adenoviral Vectors

"Deleted" adenoviral vectors have been described as first-generation vectors which have loxP recognition sequences of bacteriophage P1 positioned in the viral genome in such a way that, on infection of Cre-expressing 293 cells, most of the viral coding sequences or all the viral coding sequences are deleted by recombination between the loxP recognition sequences. The genome size of these vectors is about 9 kb. The capacity for uptake of foreign DNA is likewise about 9 kb (Lieber et al., J. Virol, 70, 8944–8960, 1996). For use in the production of deleted adenoviral vectors, the Cre recombinase gene of bacteriophage P1 is introduced by transfection together with a selection marker into the E1A- and E1B-expressing amniocytic cell line. Cell clones which, in addition to expression of E1A and E1B functions, also express the Cre function of bacteriophage P1 can then be used to produce the particular deleted Ad vector.

e) Production of Tropism-modified Gene Transfer Vectors

In a preferred embodiment, the permanent amniocytic cell line is used to produce tropism-modified gene transfer vectors. The tropism of a virus and of a viral vector derived from this virus decides whether a particular cell type can be successfully transduced with a vector or not. Uptake of a gene transfer vector into a cell is the first step for successful gene transfer into this cell. The tropism of a viral vector is thus an essential factor for efficient in vitro or in vivo gene transfer into a particular cell or into a tissue. Interaction of the surface of a viral vector (of the capsid in the case of adenoviral or AAV vectors, of the virus envelope in the case of retroviral or lentiviral vectors) with the cell membrane of a target cell is necessary for uptake into a particular cell. Although the exact mechanism of uptake of a viral vector into a target cell sometimes varies between different vectors, in all cases the interaction of surface structures of the viral vector (usually protein ligands) with structures on the target cell (usually receptors or adhesion molecules) plays an essential part. Uptake of adenoviral vectors takes place, for example, by receptor-mediated endocytosis. This entails parts of the adenoviral capsid binding to cellular receptors. In the case of adenoviral vectors derived from Ad2 or Ad5, according to the current state of knowledge there is usually binding of part of the knob domain of the fiber proteins to the coxsackie adenovirus receptor (CAR) and part of the penton base to $\alpha v\beta 3$ or $\alpha v\beta 5$ integrins. The binding of the knob domain on CAR is, according to the current state of knowledge, necessary for adhesion of the vector to the cell membrane of the target cell, whereas binding of the penton base to integrins is necessary for internalization of the vector into the target cell.

Amniocytic cell lines can be used to produce tropism-modified vectors. This applies, for example, to the production of first- and second-generation adenoviral vectors, to adenoviral vectors of large DNA capacity, to deleted adenoviral vectors, to chimeric adenoviral vectors, to AAV vectors, to retroviral and/or lentiviral vectors. Various strategies can be used to produce tropism-modified vectors in amniocytic cell lines. The strategy used for the particular tropism modification may vary for different vectors (for example adenoviral vector, AAV vector, retroviral vector). It is common to the various strategies that the surface of the particular vector (virus capsid in the case of adenoviral and AAV vectors, virus envelope in the case of retroviral and lentiviral vectors) is altered so that the binding of the vector to the target cell is altered. Examples of modifications for adenoviral vectors are:

a) Exchange of fiber proteins between different serotypes: this results in adenoviral vectors whose capsid carries a fiber protein of a different serotype. Examples thereof are exchange of the natural fiber protein of adenoviral vectors derived from serotype 2 by a fiber protein derived from serotype 17 (Zabner et al., J. Virol. 73, 8689–8695, 1999) or from serotype 9 (Roelvink et al., J. Virol. 70, 7614–7621, 1996). Other examples are exchange of the natural fiber protein of adenoviral vectors derived from serotype 5 by a fiber protein derived from serotype 7a (Gall et al., J. Virol. 70, 2116–2123, 1996) or from serotype 3 (Stevenson et al., J. Virol. 71, 4782–4790, 1997; Krasnykh et al., J. Virol. 70, 6839–6846, 1996; Douglas et al., Neuromuscul. Disord. 7, 284–298, 1997).

b) Removal of the fiber protein: the fiber protein can be removed by processes of genetic manipulation so that uptake of the vector takes place solely via interaction of the penton base or of the hexon protein (Falgout et al., J. Virol. 62, 622–625, 1988; Legrand et al., J. Virol. 73, 907–919, 1999).

c) Modification of the C terminus of the fiber protein with a peptide: examples thereof are modification of the C terminus with a polylysine peptide (Yoshida et al., Hum. Gene Ther. 9, 2503–2515, 1998: Wickham et al., Nat. Biotechnol. 14, 1570–1573, 1996; Wickham et al., J. Virol. 71, 8221–8229, 1997), a polyhistidine peptide (Douglas et al., Nat. Biotechnol. 17, 470–475, 1999) or a gastrin-releasing peptide (Michael et al., Gene Ther. 2, 660–668, 1995).

d) Modification of parts of the knob domain of the fiber protein by insertion of a peptide: examples thereof are insertion of a FLAG epitope (Krasnykh et al., J. Virol. 72, 1844–1852, 1998) or insertion of an RGD peptide (Dmitriev et al., J. Virol. 72, 9706–9713, 1998; Kasono et al., Clin Cancer Res. 5, 2571–2579, 1999).

e) Modification of the penton base: one example thereof is replacement of an RGD motif within the penton base by an LDV motif with the aim of mediating binding of the vector to $\alpha 4\beta 1$ integrins (Wickham et al., Gene Ther. 2, 750–756, 1995).

f) Modification of the hexon protein: one example thereof is insertion of an epitope derived from poliovirus type 3 (Crompton et al., J. Gen. Virol. 75, 133–139, 1994).

An alternative strategy which can be used to alter the tropism of vectors produced in amniocytic cell lines is based on the use of ligands which mediate binding of the vector to cell membrane structures such as, for example, cellular receptors or adhesion molecules. These ligands may be peptides, proteins or else antibodies. The ligands can be linked to the surface of the vectors by various processes. The linkage of the ligands to the surface of the vectors (of the capsids in the case of adenoviral or AAV vectors) can be produced by using antibodies or by a chemical crosslinking reaction. On use of antibodies it is possible to use antibodies whose specificity is directed against the capsid of the vector (for example against the knob domain of the fiber protein). Alternatively, it is possible to use antibodies whose specificity is directed against an epitope which has been introduced as neoepitope (for example a FLAG epitope or a myc epitope) into the capsid of the vector. Examples thereof are well known to the skilled worker. Examples of the use of bispecific antibodies are described in Wickham et al., J. Virol. 70, 6831–6838, 1996 (anti-FLAG/anti-α-integrin); in Wickham et al., Cancer Immunol. Immunther. 45, 149–151, 1997; Harari et al., Gene Ther. 6, 801–807, 1999 (anti-FLAG/anti-E-selectin) for transduction of endothelial cells; in Miller et al., Cancer Res. 58, 5738–5748, 1998; Blackwell et al., Arch. Otolaryngol. Head Neck Surg. 125, 856–863, 1999 (anti-Ad/anti-EGFR) for transduction of tumor cells; in Wickham et al., J. Virol. 71, 7663–7669, 1997 (anti-FLAG/anti-CD3) for transduction of T cells; in Tillman et al., J. Immunol. 162, 6378–6383, 1999 (anti-CD40/anti-Ad) for transduction of dendritic cells. Examples of the use of single-chain antibodies with specificity for one virus capsid determinant which is coupled to a ligand are described in Watkins et al., Gene Ther. 4, 1004–1012, 1997; in Goldman et al., Cancer Res. 57, 1447–1451, 1997; Rancourt et al., Clin. Cancer Res. 4, 2455–2461, 1998; Gu et al., Cancer Res. 59, 2608–2614, 1999; Rogers et al., Gene Ther. 4, 1387–1392, 1997 (anti-Ad/FGF2) for transduction of FGF2-receptor-expressing tumor cells; in Douglas et al., Nat. Biotechnol. 14, 1574–1578, 1996; Douglas et al., Neuromuscular Disord. 7, 284–298, 1997 (anti-Ad/Folat) for transduction of tumor cells which express the folic acid receptor on the cell surface.

In the case of gene transfer vectors in which the natural tropism has been abolished and replaced by another tropism, for example by introducing a ligand into the knob domain of the fiber protein of Ad5, it may be necessary to modify a permanent amniocytic cell line by the preferably stable expression of a receptor which recognizes this new ligand (Douglas et al., Nat. Biotechnol. 17, 470–475, 1999). It is likewise possible for the permanent amniocytic cell line to be used to produce gene transfer vectors which have a defect in the production of one or more structural proteins. This is done by complementing the particular defects of the gene transfer vector in the permanent amniocytic cell line. For example, an adenoviral vector which has a mutation in the gene coding for the fiber protein can be produced in an amniocytic cell line which complements the defect in the fiber protein. This is achieved by introducing a fiber expression cassette into the amniocytic cell line and stable or inducible expression of the fiber protein in this amniocytic cell line (Von Seggern et al., J. Gen. Virol. 79, 1461–1468, 1998). The fiber protein expressed in the amniocytic cell line may be a natural, unmodified fiber protein or else an altered, for example tropism-modified, fiber protein (Von Seggern et al., supra). It is also possible to produce adenoviral vectors completely lacking the fiber protein in the permanent amniocytic cell line (Legrand et al., J. Virol., 73, 907–919, 1999; Von Seggern et al., J. Virol. 73, 1601–1608, 1999).

The use of E1A- and E1B-expressing amniocytic cell lines is to be preferred because, in contrast to 293 cells, no generation of replication-competent vectors can take place by homologous recombination. In a particular embodiment of the aspect of the use of an amniocytic cell line for producing gene transfer vectors, this cell line is the cell line according to the invention.

Therapeutic Genes

The products of the genes, in particular of the therapeutic genes, which can be encoded and expressed by vectors produced in transformed amniotic cells, that is to say a permanent amniotic cell line, can be, for example, any muscle proteins, coagulation factors, membrane proteins or cell cycle proteins. Examples of proteins which can be expressed by vectors produced in transformed amniocytes are dystrophin (Hoffman et al., Cell 51, 919, 1987), factor VIII (Wion et al., Nature 317, 726 1985), cystic fibrosis transmembrane regulator protein (CFTR) (Anderson et al., Science 251, 679, 1991), ornithine transcarbamylase (OTC) (Murakami et al., J. Biol. Chem., 263, 18437, 1988), alphal-antitrypsin (Fagerhol et al., in: Hum. Genet., vol. 11, Harris ed., Plenum, New York, p. 1, 1981). The genes coding for proteins are known and can be cloned from genomic or cDNA banks. Examples of such genes are the dystrophin gene (Lee et al., Nature 349, 334, 1991), the factor VIII gene (Toole et al., Nature 312, 342 1984), the CFTR gene (Rommens et al., Science 245, 1059, 1989, Riordan et al., Science 245, 1066, 1989), the OTC gene (Horwich et al., Science 224, 1066, 1984), and the alphal-antitrypsin gene (Lemarchand et al., Proc. Natl. Acad. Sci. USA, 89, 6482, 1992).

Examples of other genes expressed by vectors which can be produced in transformed amniocytes are the p53 gene for treating oncoses (Wills et al., Hum. Gene Ther. 5, 1079, 1994, Clayman et al., Cancer Res. 55, 1, 1995), the Rb gene for treating vascular proliferative disorders (Chang et al., Science 267, 518, 1995), or the thymidine kinase gene of herpes simplex virus (HSV) type 1 for the therapy of oncoses. The gene expressed by vectors produced in transformed amniocytes does not necessarily code for a protein. Thus, for example, it is possible for functional RNAs to be expressed. Examples of such RNAs are antisense RNAs (Magrath, Ann. Oncol. 5, Suppl 1), 67–70 1994, Milligan et al., Ann. NY Acad. Sci. 716, 228–241, 1994, Schreier, Pharma. Acta. Helv., 68, 145–159 1994), and catalytic RNAs (Cech, Biochem. Soc. Trans. 21, 229–234, 1993; Cech, Gene 135, 33–36, 1993; Long et al., FASEB J. 7, 25–30, 1993; Rosi et al., Pharm. Therap. 50, 245–254, 1991).

Vectors produced in transformed amniocytes may, in addition to the therapeutic gene, comprise any reporter gene in order to be able to follow expression of the vector better. Examples of reporter genes are known in the prior art and include, for example, the β-galactosidase gene (Fowler et al., Proc. Natl. Acad. Sci. USA 74, 1507, 1977).

Vectors which can be produced in transformed amniocytes may comprise more than a single gene. The maximum number of genes which can be produced in such vectors depends on the uptake capacity of the particular vector and on the size of the genes.

The choice of the promoters which control expression of the therapeutic genes of vectors produced in transformed amniocytes is not critical. Viral or nonviral promoters which show constitutive, tissue-specific or regulable activity can be used for expressing a protein or a functional RNA. The SV40 or cytomegalovirus promoter (Andersson et al., J. Biol. Chem. 264, 8222–8229, 1964) can be used, for example, for constitutive expression of a gene. The use of the muscle creatine kinase (MCK) promoter permits tissue-specific expression of a protein or of a functional RNA in skeletal muscle and myocardium. Gene expression can be controlled quantitatively and qualitatively by the use of a regulable system (Furth et al., Proc. Natl. Acad. Sci. USA 91, 9302–9306, 1994).

It is possible to include in vectors which can be produced in transformed amniocytes genetic elements which influence the behavior of the vector inside the recipient cell. Examples of such elements are elements which facilitate nuclear targeting of the vector DNA (Hodgson, Biotechnology 13, 222–225, 1995).

Vectors produced in this way can be used in vitro or in vivo. An in vitro gene transfer takes place outside the body, for example by adding the vector to cells in culture or to primary cells which have been taken from the body for the purpose of gene transfer. In the case of in vivo gene transfer, vector particles can be applied in various ways depending on the tissue which is to be transduced. Examples are injection into the arterial or venous vascular system, direct injection into the relevant tissue (for example liver, brain, muscle), instillation into the relevant organ (for example lung or gastrointestinal tract) or direct application onto a surface (for example skin or bladder).

The following figures and example are intended to illustrate the invention in detail without restricting it thereto.

DESCRIPTION OF THE FIGURES

FIG. 4 shows, listed in a table, the production of a first-generation adenoviral vector in various cloned cell lines on the basis of bfu (blue forming units) per cell and the efficiency of transfection of the appropriate cell lines on the basis of plaque formation.

FIG. 6 shows the time course of the synthesis of recombinant adenoviral vectors in two cloned cell lines N52.E6 and N52.F4.

DETAILED DESCRIPTION OF THE INVENTIONS

EXAMPLES

1. Clonings

Figures 1, 1A:
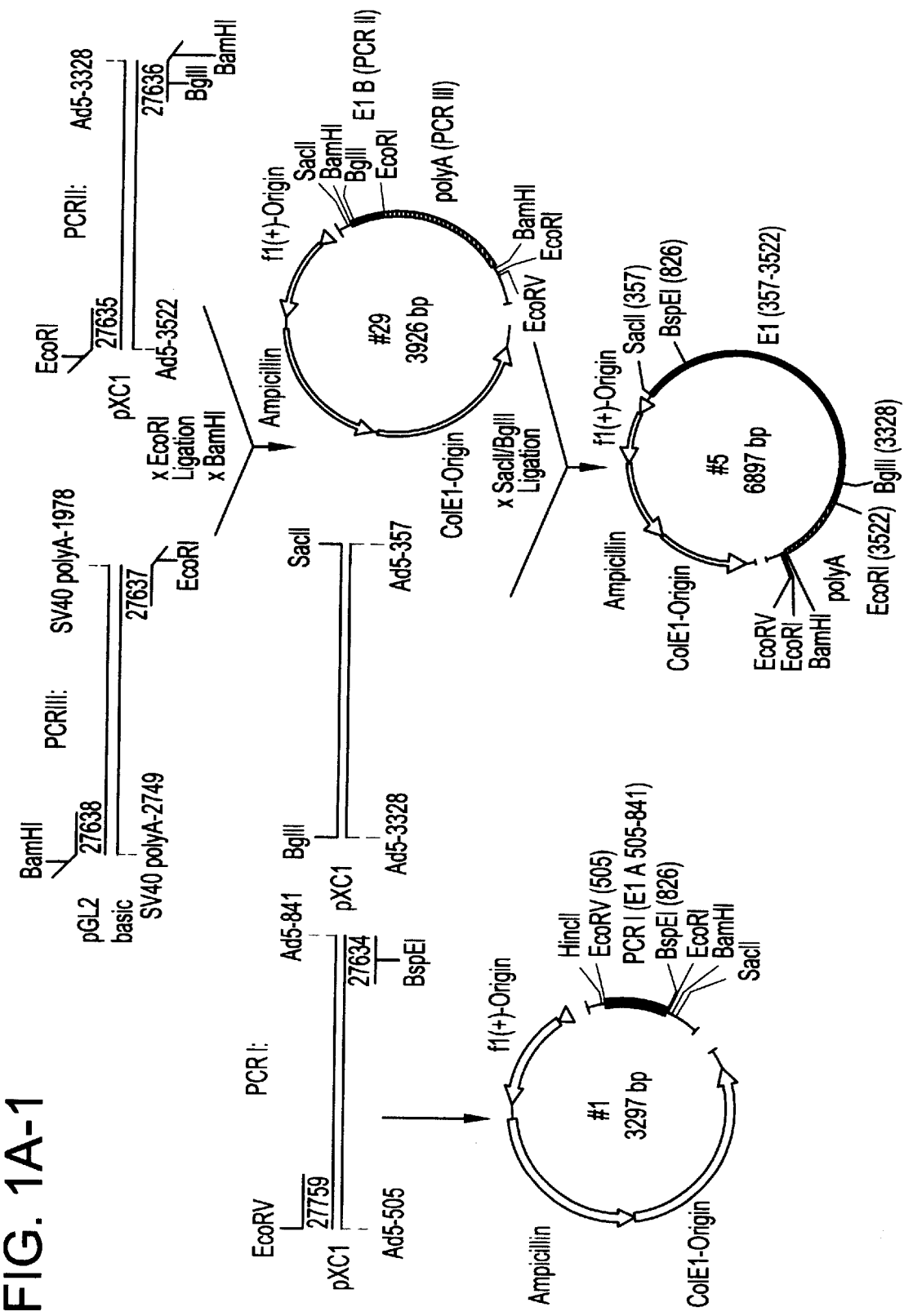
FIG. 1 shows a summary of the clonings.
FIG. 1A depicts diagrammatically the cloning steps for plasmid STK146.
Figures 1, 1A, 2:
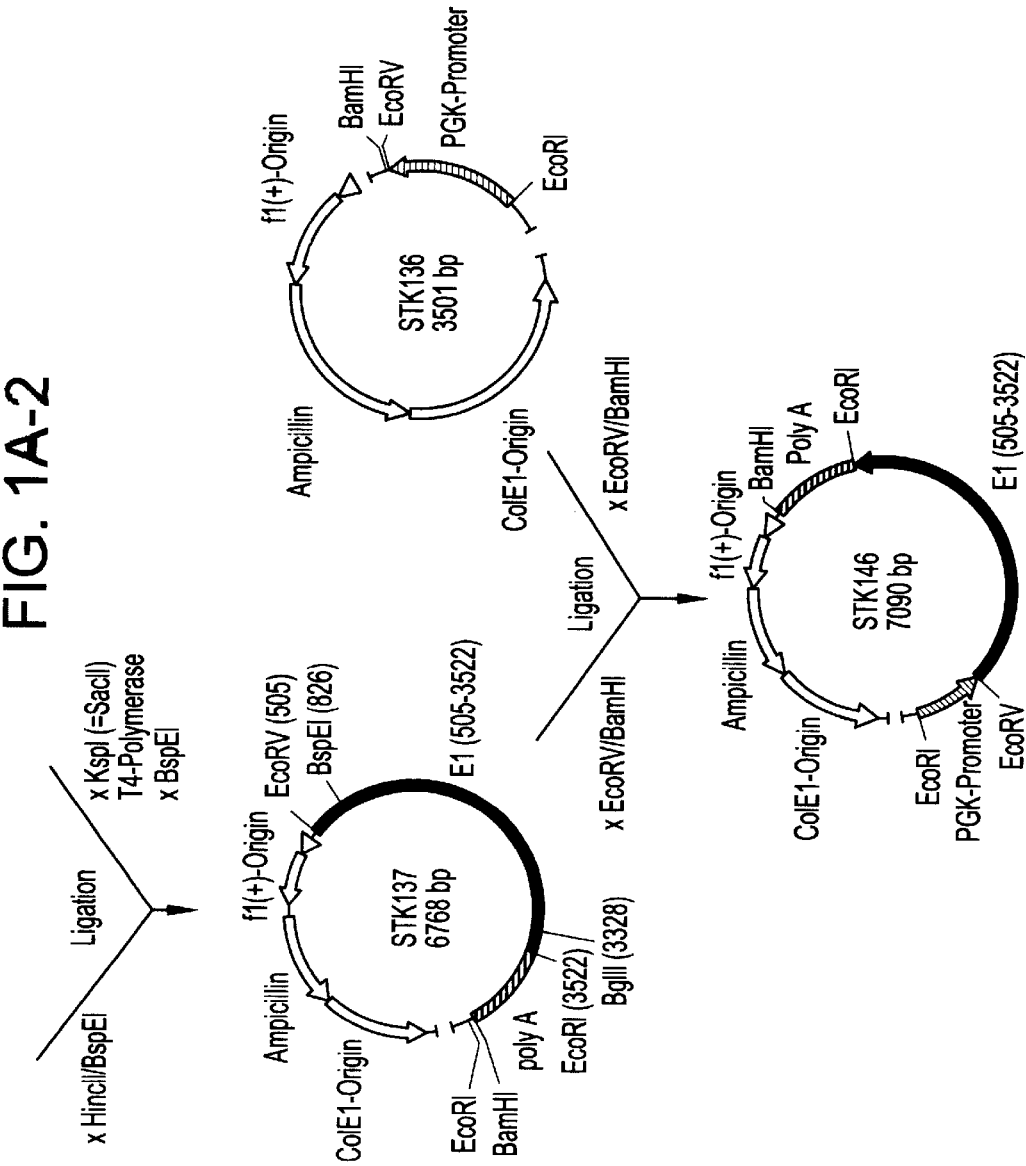
FIG. 2 shows the cell islets (FIG. 2B and FIG. 2B) obtained from amniocytes by transformation by adenoviral E1 functions, and the cell lines N52.E6 (DSMZ ACC2416.
Figure 1B:
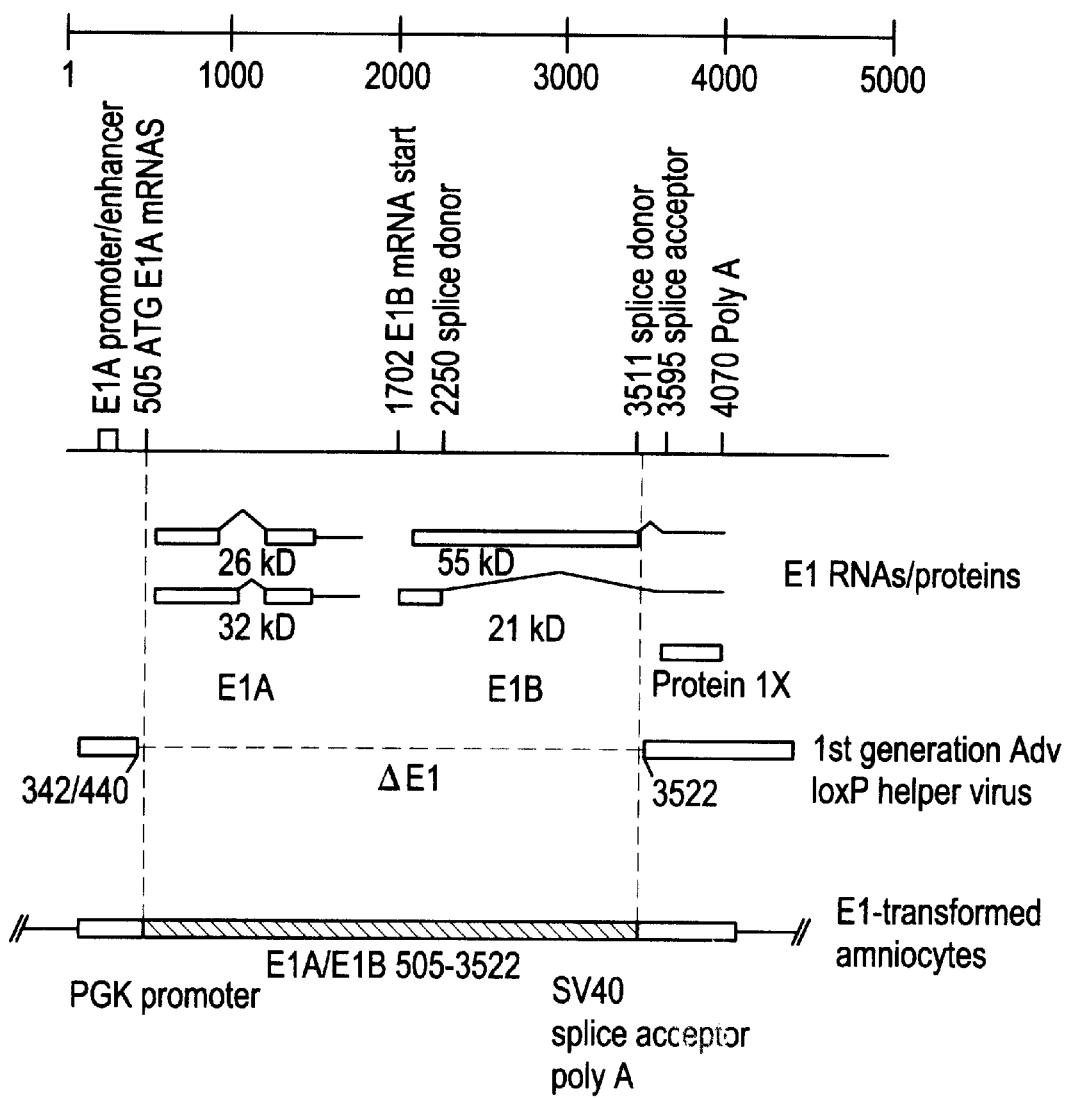
FIG. 1B depicts the left-terminal approx. 15% of the genome of adenovirus type 5, including the E1 RNAs, the coding regions, the starting points of E1A and E1B transcription, and the splice donor and splice acceptor sites and polyadenylation sequences which are important for the cloning. It is important that the splice donor site at base pair 3511 of Ad5 has been retained in the cloning for plasmid STK146, but that the splice acceptor site and the polyadenylation signal have been replaced by corresponding functions of SV40. In addition, the E1A promoter of Ad5 has been replaced by the PGK promoter. Thus STK146 contains the Ad5 sequences from base pair 505–5322 and the cell lines transformed with this plasmid contain no Ad5 sequences which are present in first- or second-generation adenoviral vectors or in loxP helper viruses.

FIG. 1 depicts a summary of the clonings.

a) Plasmid STK136

Plasmid STK 136 contains the murine phosphoglycerate kinase promoter (seq. No. 1; Adra et al., Gene 60, 65–74, 1987) in pBluescript KsII (Stratagene) and was produced as follows:

3.5 µg of plasmid PGK-hAAT (Kay et al., Hepatology 21, 815–819, 1995) were digested with EcoRV and fractionated by size in a 1.5% agarose gel. The 0.5 kb band containing the PGK promoter fragment which was sought was, after staining in ethidium bromide, cut out and the DNA was electroeluted. At the same time, pBluescript KSII was digested with EcoRV and HincII, and the free DNA ends were dephosphorylated. After subsequent phenol/chloroform extraction and ethanol precipitation, equimolar amounts of these DNA fragments were ligated and transformed into ultracompetent XL-2 Blue bacteria (Stratagene). The plasmid clones were characterized by means of a restriction digestion, and the plasmid resulting therefrom was called STK136 (isolate #6).

b) Plasmid STK137

Plasmid STK137 contains the complete E1 expression cassette of Ad5 including the 3' splice and polyadenylation signals from SV40 and was produced as follows:

PCR Amplification of the Ad5 Sequence bp 505–841 (PCR I) (Seq. No. 2)

10 ng of the plasmid pXC1 (Microbix) were amplified together with 400 ng each of the oligonucleotides 27759 (Seq. No. 3) and 27634 (Seq. No. 4), 0.2 mM dNTPs and 1.25 U Pfu polymerase in 10 mM KCl, 10 mM $(NH_4)_2SO_4$, 20 mM Tris/HCl, pH 8.75, 2 mM $MgSO_4$, 0.1% Triton X-100, 100 µg/ml BSA under the following conditions:

I   10 minutes at 94° C.,
II  1 minute at 94° C.,
    2 minutes at 50° C.,
    3 minutes at 72° C.,
III 10 minutes at 72° C..

Repeating step II in 15 cycles. The DNA was purified using the QIAquick PCR purification kit (Qiagen) as stated by the manufacturer and was precipitated with ethanol.

To clone the PCR fragment, 2.5 µg of pBluescript KSII were digested with EcoRV, and the free DNA ends were dephosphorylated, ligated in equimolar amounts with the PCR fragment and transformed into XL-2 Blue cells. The plasmid resulting therefrom is referred to as #1 hereinafter. PCR Amplification of the Ad5 Sequence bp 3328–3522 (PCR II) Seq. No. 5)

10 ng of the plasmid pXC1 (Microbix) were amplified together with 400 ng each of the oligonucleotides 27635

(Seq. No. 6) and 27636 (Seq. No. 7) under the conditions described above. After the PCR, the DNA was extracted with phenol/chloroform, precipitated with ethanol, digested with EcoRI, again extracted with phenol/chloroform, precipitated and dissolved in 30 µl of TE.

PCR Amplification of the 3' Splice and Polyadenylation Signal from SV40 with the Aid of the Plasmid pGL2-Basic bp 1978–2749 (PCR III) (Seq. No. 8)

20 ng of the plasmid pGL2-Basic (Promega, GenBank/EMBL Acc. No.: X65323) were amplified together with 800 ng each of the oligonucleotides 27637 (seq. No. 9) and 27638 (seq. No. 10), 0.4 mM DNTPS and 2.5 U of Pfu polymerase under the conditions described above. After the PCR, the DNA was extracted with phenol/chloroform, precipitated with ethanol, digested with EcoRI, again extracted with phenol/chloroform, precipitated in ethanol and dissolved in 30 µl of TE. Then 10 µl each of DNA from PCR II and III were ligated in a volume of 50 µl, extracted with phenol/chloroform, precipitated with ethanol and digested with BamHI in a volume of 100 µl. After renewed phenol/chloroform extraction and ethanol precipitation, the DNA was ligated with equimolar amounts of pBluescript KSII DNA which had previously been digested with BamHI. and dephosphorylated. The plasmid resulting therefrom is referred to as #29 hereinafter. For further cloning, 3.5 µg of plasmid DNA #29 were digested with SacII and BglII, dephosphorylated, extracted with phenol/chloroform and precipitated in ethanol. At the same time, 3.5 µg of pXC1 were digested with BglII and SacII, and the 2.9 kb fragment was fractionated by electrophoresis and electroeluted. Equimolar amounts of the two DNAs were ligated and transformed into XL-2 Blue cells. The plasmid resulting therefrom is referred to as #5 hereinafter. For the final cloning of STK137, plasmid #1 was digested with HincII and BspEI and fractionated by electrophoresis, and an approx. 350 bp fragment was electroeluted. As vector DNA, plasmid #5 was digested with KspI (isoschizomer of SacII), the ends were filled in with T4 polymerase, and phenol/chloroform extraction and ethanol precipitation were carried out. The DNA was then digested with BspEI, the ends were dephosphorylated, and phenol/chloroform extraction and ethanol precipitation were again carried out. The two DNAs were ligated and transformed into XL-2 Blue cells. The plasmid resulting therefrom was called STK137 (isolat #34).

c) Plasmid STK146 (Seq. No. 18)

Plasmid STK146 contains the murine PGK promoter, the complete E1 region of Ad5 (bp 505–3522) and the 3' splice and polyadenylation signal of SV40.

For the cloning, 4 µg of STK137 were digested with EcoRV and BamHI and fractionated by electrophoresis, and the 3.7 kb fragment was electroeluted. In addition, 3.3 µg of STK136 were digested with EcoRV and BamHI, dephosphorylated, phenol/chloroform extracted and precipitated with ethanol. Equimolar amounts of the two plasmids were ligated and transformed into XL-2 Blue cells. The plasmid resulting therefrom was called STK139. Final sequence analysis of STK139 revealed a mutation at the bp 2613 (the numbering in this connection refers to the Ad5 DNA sequence), which led to a tyrosine to asparagine amino acid exchange (2613 TAC→GAC). For this reason, the fragment containing the mutation in STK139 was replaced by the BstEII (bp 1915)-BglII (bp 3328) fragment from pXCl. This was done by digestion of STK139 with BstEII and BglII, dephosphorylation, phenol/chloroform extraction, ethanol precipitation, fractionation by electrophoresis and electroelution of the 5.8 kb fragment. pXCl was likewise digested with BstEII and BglII and fractionated by electrophoresis, and the 1.4 kb fragment was electroeluted. After ligation and transformation, DNA from 4 plasmid clones was sequenced; two of them contained the correct sequence at bp 2613. Isolate number 2 was sequenced completely and is referred to as STK146 hereafter.

Sequence Analysis of STK146

500 of STK146 #2 were sequenced with 10 pmol of the following sequence primers under standard conditions:

Primer

28231 Ad5 nt. 901–920 (Seq. No. 11)

28232 Ad5 nt. 1301–1320 (Seq. No. 12)

28233 Ad5 nt. 1701–1720 (Seq. No. 13)

28234 Ad5 nt. 2100–2119 (Seq. No. 14)

28235 Ad5 nt. 2500–2519 (Seq. No. 15)

28236 Ad5 nt. 2853–2872 (Seq. No. 16)

28237 Ad5 nt. 3249–3268 (Seq. No. 17)

2. Cultivation of Primary Amniocytes and Cell Lines

All the cell culture reagents, media and sera were purchased from GIBCO Life Technologies. The cell line 293 which as used as control in some experiments was cultivated in modified Eagle's medium (MEM) with 10% fetal calf serum (FCS), 1× penicillin/streptomycin at 37° C. (100×, Cat# 10378-016), 95% humidity and 5% $CO_2$. The new E1-transformed cell lines were produced using primary fetal cells which had been obtained from amniotic fluid by amniocentesis as part of prenatal diagnosis. After the biopsy, the cells were seeded by routine methods in plastic culture bottles and cultivated in Ham's F10 medium (nutrient mixture Ham's F10 with L-glutamine, Cat# 31550-023), 10% FCS, 2% Ultroser® G, 1× antibiotic/antimycotic solution (100×, Cat# 15254-012). 2.5 µg/ml Fungizione® (amphotericin B, Cat# 15290-018). Some of the cells adhered to the base of the cell culture bottle and proliferated. Sufficient cells for chromosome analysis were available after about 2 weeks. After establishment of the karyotype, amniocyte cultures with numerically and structurally normal chromosomes were used to produce the cell line. Cells from three different sources, taken by amniocentesis either 3, 6 or 7 weeks beforehand, were used in various experiments. The nutrient medium used was Ham's F10 medium, 10% FCS, 2% Ultroser®Cr, 1×antibiotic/antimycotic solution, 2.5 µg/ml Fungizione®. The culture conditions were 37° C., 95% humidity and 5% $CO_2$. Seven days after transfection, the amniocytes were cultivated further in Ham's F10 medium, 10% FCS, 1×penicillin/streptomycin. After the generation of single-cell clones, these were transferred to new dishes and cultivated further in alpha-MEM with 10% FCS, 1× penicillin/streptomycin.

3. Transfection and Transformation of Amniocytes

Figure 2A:
FIG. 2C) and N52.F4 (FIG. 2D) cloned from single cells. This time it should be noted that the cell lines and single cell clones differ morphologically from the amniocytes in that they are usually smaller and there is no contact inhibition of their growth.
Figure 2C:
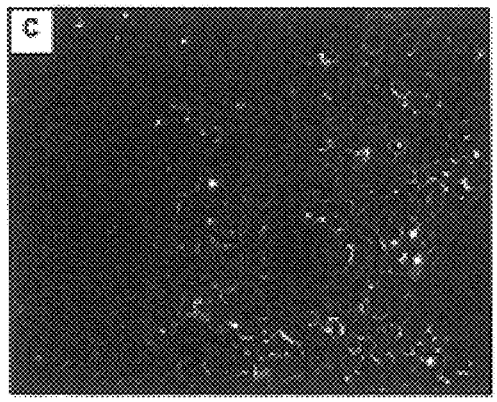
Figure 2B:

For the transfection, the amniocytes were seeded on cell culture dishes (diameter 60 mm, surface area 22.1 $cm^2$) at a density of 2–5×$10^5$ per dish and transfected the following day. For the transfection, 20 µg of plasmid STK146 were digested with ScaI, extracted with phenol/chloroform, precipitated with ethanol and taken up in 20 µl of TE, which gave a DNA concentration of 0.5 µg/µl. In the initial experiments, amniocytes were transfected 3 or 7 weeks after removal, in 5 dishes each, with the Effectene transfection kit as stated by the manufacturer (Qiagen) as follows:

4 µl of STK146 digested with ScaI were mixed with 146 µl of EC buffer. After addition of 8 µl of enhancer, the solution was briefly vortexed and incubated at room temperature for 5 minutes. Then 25 µl of Effectene were added and, after vortexing for 10 seconds, incubated at room temperature for a further 10 minutes. During this, the medium was cautiously aspirated off the cells and replaced by 4 ml of fresh nutrient medium (see Section 2. above). After the incubation was complete, the transfection mixture was mixed with 1 ml of fresh nutrient medium and cautiously added dropwise to the cells. The cells were cultivated further as described above. Seven days after the transfection, the cells in each dish were transferred to a larger dish (diameter 150 mm, surface area 147.8 cm$^2$). This was done by cautiously aspirating off the medium, and the cells being washed with PBS, detached in trypsin and transferred to a new dish and cultivated further as described in Section 2. 18 to 22 days after the transfection clonal cell islets were clearly to be seen and were clearly distinguished morphologically from the amniotic cells (FIGS. 2A, 2B). The main proportion in an untransformed amniocyte culture consists of larger cells which show contact inhibition of their growth. Cells in transformed single-cell colonies are very much smaller, grow much more quickly and show no contact inhibition of their growth. They grow as cell islets consisting of smaller cells which are crowded tightly together, and are unambiguous under the light microscope and can be identified without difficulty. These cell islets were picked and transferred to a new dish (diameter 60 mm) containing the medium described above. After further growth, the cell lines were transferred to 147.8 cm$^2$ cell culture dishes and cultivated further as described under 2. After the first transfer to 147.8 cm$^2$ cell culture dishes, the cell passages were counted. Initially, about 40 cell clones from the cells which had been transfected 3 and 7 weeks after removal were cultivated further. Subsequently, that is to say after prolonged cultivation, there was a drastic change in the morphology of some of the cell clones, and they showed instability in their growth characteristics. The further experiments were restricted to further cultivation and analysis of eight morphologically stable cell lines. These were referred to as follows: GS.A55 (produced from amniocytes transfected 3 weeks after removal), GS.N21, GS.N24, GS.N27, GS.N49, GS.N51, GS.N52, GS.N53 (produced from amniocytes transfected seven weeks after removal).

During the first passages all the cell clones showed a comparable morphology, but this was changed by subsequent passages. Thus, for example, some cell clones changed to assume a highly rounded shape and, after further passages, they were no longer adherent. Other cell clones showed extensive vacuolization, but this did not appear to have any effect on their growth. After the single-cell cloning, all the cell lines showed a uniform morphology and, for example, N52.EG and N52.F4 had an epithelial appearance. They were comparable to 293 cells in their growth rate and cell density.

4. Efficiency of the Transformation

In order to determine the efficiency of the transformation by the E1 functions more accurately, seven new dishes each containing 2–5×10$^5$ cells were transfected as described in Section 3. The cells were transferred only 24 hours after the transfection to dishes 147.8 cm$^2$ in size and were cultivated further in Ham's F-10 medium, 10% fetal calf serum, 2% Ultroser® G, 1× antibiotic/antimycotic solution, 2.5 μg/ml Fungizione for 5 days and in Ham's medium, 10% fetal calf serum, 1× penicillin/streptomycin solution for a further 25 days. A dish with untransfected cells was cultivated under the same conditions as a control. During this time, the morphologically clearly distinguishable (see FIGS. 2A, B) colonies resulting from single transformation events were counted. Single-cell clones could be counted on all the cell culture dishes apart from the untransfected control dish. On average there were 4 cell clones per plate, which corresponded to a transformation efficiency of 1 in 0.5–1×10$^5$ cells.

5. Single-cell Cloning

Figure 2D:

As already mentioned, some of the cell lines showed different morphological characteristics, which is why up to ten single cell lines were set up from each cell line. The passages for the individual cell lines differed in these cases: GS.A55: P17, GS.N21: P24, GS.N24: P20, GS.N27: P19, GS.N49: P21, GS.N51: P39, GS.N52: P22, GS.N53: P20. For this purpose, the cells were detached from the cell culture dishes and, at a concentration of 5×10$^6$ cells/ml, diluted 1:1000, 1:50,000 and 1:500,000 in nutrient medium. 100 μl cells from all the-dilutions were seeded onto 96-well plates, and the cell clones which had unambiguously resulted from single cells were cultivated further. FIG. 2C shows the cell line GS.N52.E6 (DSMZ No.), and FIG. 2D shows cell line GS.N52.F4; both cell clones are derived from the original cell line GS.N52.

6. Characterization of the E1 Cell Lines a) Southern Blot Analyses

Figure 3:
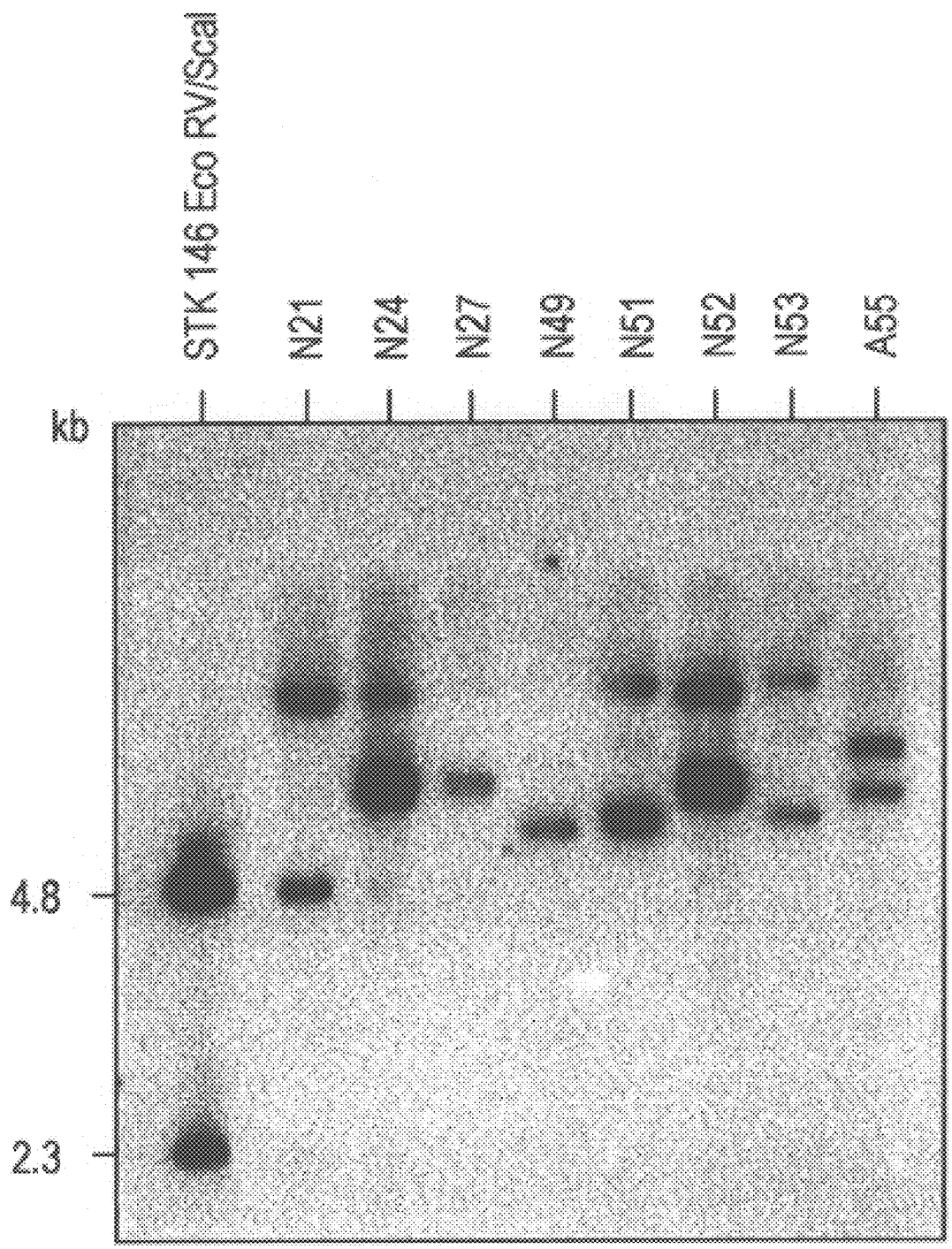
FIG. 3 shows the integration status of STK146 in eight different E1-transformed amniocytic cell lines by means of a Southern blot.

Southern blot analyses were carried out in order to investigate the integration status of the E1region in the cell lines. This was done by isolating genomic DNA from all eight E1 amniotic clones (see Section 5.), and 5 μg of each were digested with EcoRV, fractionated by electrophoresis and transferred to a nylon membrane. EcoRV cuts once in the E1 expression cassette. Hybridization with radiolabeled STK146 DNA confirmed integration of 1–2 copies of STK146 in all clones. FIG. 3 shows the integration pattern in the E1 cell clones. There are mainly two high molecular weight bands evident for all the clones, which indicates integration of a single copy. The cell clones GS.N24 and GS.N52 each showed an additional band with relatively strong intensity, which might indicate integration of tandem copies of STK146. For none of the cell clones were there any bands smaller than STK146 digested with ScaI and EcoRV, which suggested that all the integrates were present completely and not deleted.

b) Generation of Recombinant Adenoviruses

After the single-cell cloning, the cell clones were tested for their ability to generate recombinant adenovirus. This was done once by infecting 3–5 single-cell clones of each cell line in approx. 70% confluent 24-well plates with about 5 MOI (multiplicity of infection) of Adβgal (recombinant first-generation adenoviral vector). 48 hours after the infection, the cells were lysed by freezing and thawing three times, and the amount of Adβgal produced was analyzed by infecting 293 cells and subsequently staining the cells (MacGregor et al., in: Gene Transfer and Expression Protocols, Murray ed. Humana, Clifton, N.J., vol. 7, pp. 217–235, (1991)) for detecting β-galactosidase production (FIG. 4). This method affords an only approximate production of recombinant adenovirus because the number of cells and therefore the amount of virus used may differ in the different cell clones because of their size and growth rate. The cell clones which gave the largest yield in this first test were analyzed more exactly in a further experiment. This was done by seeding about 3×10$^7$ cells on 3 dishes (diameter 100 mm, surface area 60 cm$^2$). The cells were counted the next day and were infected with exactly 5 MOI of Adβgal based on the number of cells found. 48 hours after the infection, the cells were harvested and lysed by freezing and thawing three times, and the amount of Adβgal produced was analyzed by infecting 293 cells and subsequently staining. The result is depicted in FIG. 4.

c) Transfection Efficiency

Some of the cloned cell lines were tested for plaque formation. This was done by transfecting approx. 70% confluent cell culture dishes (diameter 60 mm) with 2 μg of infectious plasmid GS66 by the calcium phosphate method. Plasmid GS66 contains the complete adenovirus genome with a deletion in the E1 region from nucleotide 440 to nucleotide 3523. The adenoviral terminal repeat sequences (ITRs) are flanked in this plasmid by SwaI restriction cleavage sites, so that infectious virus and plaques can be produced after transfection of SwaI-digested plasmid. About 24 hours after transfection, the cells were covered with about 10 ml of MEM, 1% agarose, 0.5× penicillin/streptomycin, 0.05% yeast extract. Plaques were visible after incubation at 37° C., 95% humidity, 5% $CO_2$ for about 1 week. FIG. 4 shows the number of counted plaques averaged for 2 independent transfections in each case.

d) Expression of E1A and E1B Functions of Ad5

Expression of the Ad5-E1A and of the E1B-21 kD proteins in the cloned cell lines was detected by Western blot analyses using monoclonal antibodies.

Figure 5:
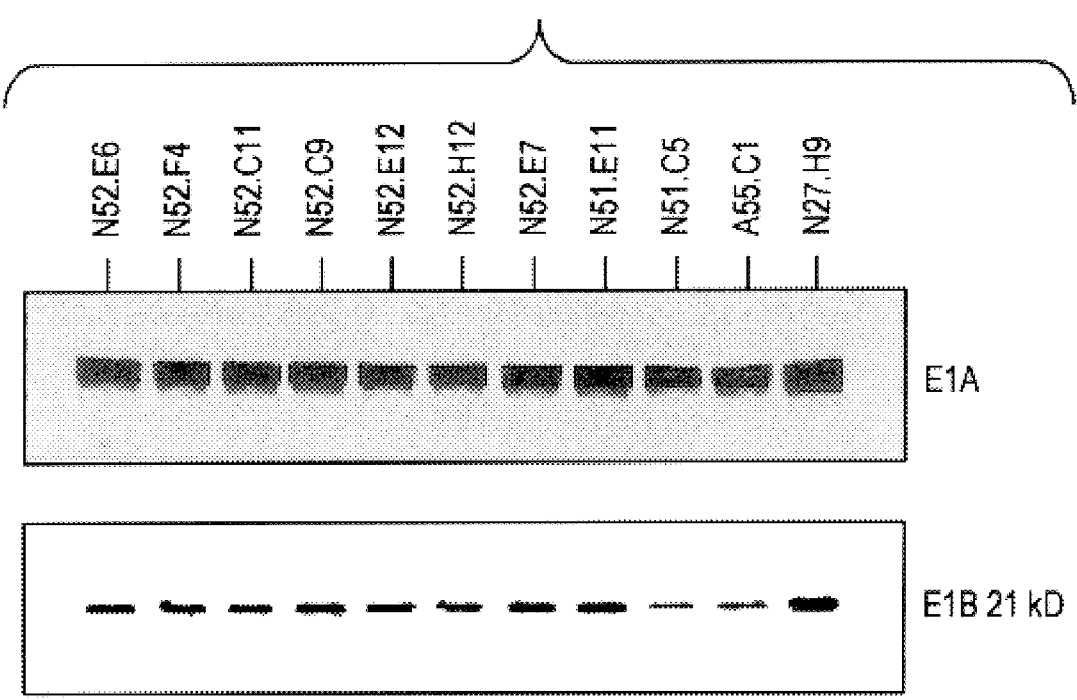
FIG. 5 shows the expression of the E1A and E1B proteins of Ad5 in eleven cloned amniocytic cell lines (Western blot).
Figure 6A:
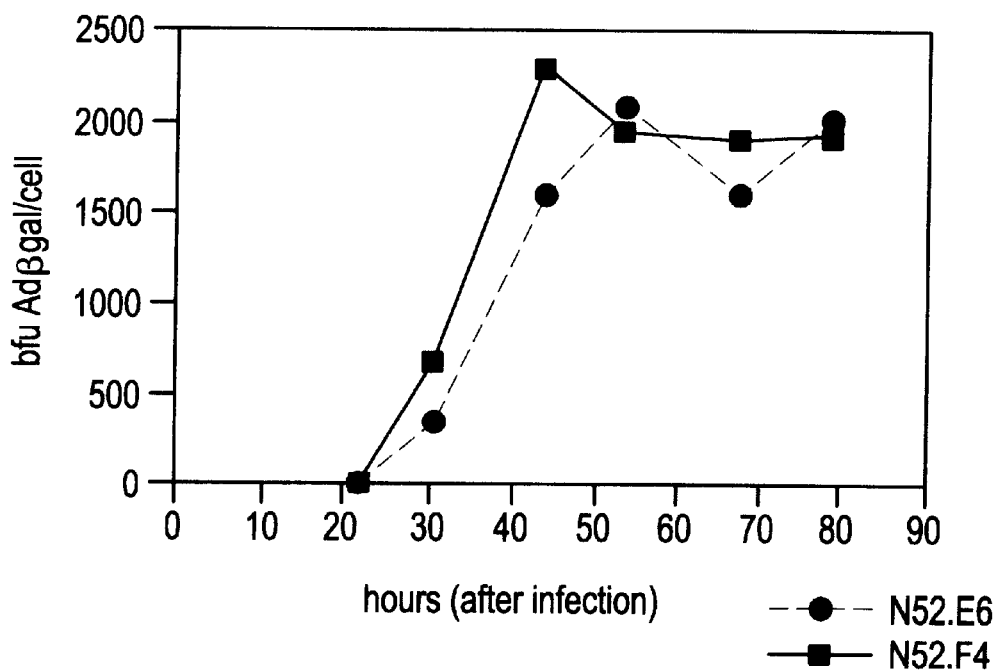
FIG. 6A shows the synthesis of a first-generation adenoviral vector.

The cells were carefully detached from a cell culture (diameter 10 cm) in PBS/1 mM EDTA, pelleted and taken up in 150 µl of 50 mM tris/HCl PH 8, 140 mM NaCl, 0.5% NP40, 4 mM EDTA, 2 mM EGTA, 0.5 mM PMSF, 5% glycerol. The cells were lyzed by additional Dounce grinding and centrifuged down at 13,000 rpm for 10 minutes, and the protein concentration in the supernatant was determined using a protein determination kit (BIORAD, Microassay Procedure). 10 µg of protein were fractionated on a 12% SDS polyacrylamide gel, transferred to a nitrocellulose membrane (Hybond ECL, Amersham Pharmacia Biotech) and incubated with an anti-E1A or anti-E1B 21 kD antibody (Calbiochem, dilution 1:300). The next day, the blot was washed and hybridized with a second anti-mouse antibody (E1A) or anti-rat antibody (E1B) to which horseradish peroxidase was coupled. The horseradish peroxidase reaction was started by incubation of equal volumes of enhance solution 1 and 2 (ECL, Amersham Pharmacia Biotech), and the photochemical reaction which developed thereby was visualized by brief exposure to an X-ray film. FIG. 5 shows the result of a Western blot analysis.

e) Time-course of the Synthesis of Recombinant First-generation Adenoviral Vectors and Adenoviral Vectors with Large DNA Capacity Two cloned cell lines N52.E6 and N52.F4 showed the highest yield of recombinant first-generation adenoviral vectors in the experiments described above. Further knowledge about the time course is important for optimal production of adenoviral vectors, especially when these cells are adapted to suspension cultures and the success of infection cannot be followed by means of a cytopathic effect. For this analysis, several dishes (diameter 6 cm) each with $3 \times 10^6$ cells were infected with 5 MOI of Adβgal and harvested at the stated times after the infection. The yield of recombinant adenovirus was again determined by infecting 293 cells, staining and counting the blue cells (FIG. 6A).

It is intended in future also to use the new cell lines for producing adenoviral vectors with large DNA capacity (see above). Production of these adenoviral vectors requires helper viruses which supply the deleted functions and proteins for a lytic infection cycle in trans. The packaging signal of these helper viruses is deleted with the aid of loxP recognition sequences and Cre recombinase, which is expressed by the cell line, on infection. It is therefore intended in future experiments that the new E1-transformed cell lines will be transfected with a Cre-expressing plasmid, and the recombinase will be expressed stably.

Figure 6B:
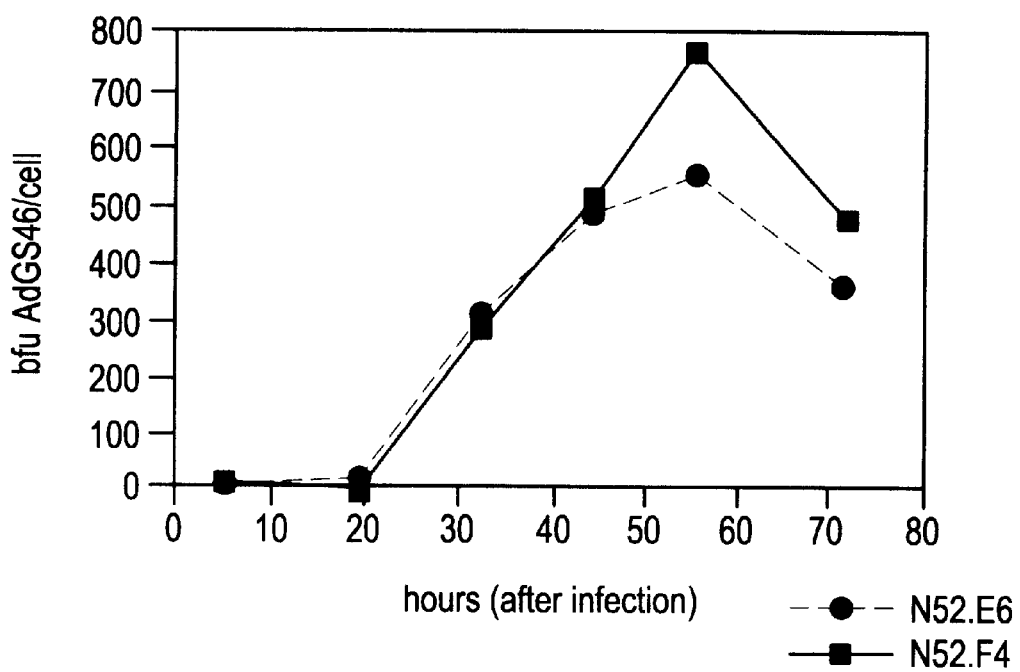
FIG. 6B shows the synthesis of an adenoviral vector with large DNA capacity.

It has been tested in preliminary experiments whether the new E1 amniocytes are also able to produce adenoviral vectors of large DNA capacity, and whether production kinetics and the amount of produced vectors corresponds to that achieved with the existing Cre-expressing 293 cells. For this purpose, several dishes each with $3 \times 10^6$ cells of the cell lines N52.E6 and N52.F4 were infected with 5 MOI of loxP helper virus and 10 MOI of AdGS46 (β-gal-expressing adenoviral vector with large DNA capacity) and harvested at the stated times after the infection. The yield of β-gal-expressing adenoviral vector with large DNA capacity was again determined by infecting 293 cells, staining and counting the blue cells (FIG. 6B). The amount of adenoviral vectors of large DNA capacity synthesized in the amniocytes corresponds to that also produced in Cre-expressing 293 cells (data not shown).

What is claimed is:

1. A permanent amniocytic cell line comprising at least one nucleic acid which brings about expression of the gene products of the adenovirus E1A and E1B regions.

2. A cell line as claimed in claim 1, wherein the at least one nucleic acid also brings about expression of the gene products of the adenovirus E2A, E2B, or E4 regions, or of Cre recombinase.

3. A cell line as claimed in claim 1, wherein expression of the gene product of the E1A region is under the control of a constitutive promoter, preferably the phosphoglycerate kinase (PGK) promoter.

4. A cell line as claimed in claim 1, wherein expression of the gene product(s) of the E1B region is under the control of an adenoviral promoter.

5. A cell line as claimed in claim 4, wherein the adenoviral promoter is an adenoviral E1B promoter.

6. A cell line as claimed in claim 1, wherein the gene products of the adenovirus E1A and E1B regions are derived from human adenovirus type 5.

7. A cell line as claimed in claim 1, wherein the cell line is a human cell line.

8. A process for producing a permanent amniocytic cell line, the method comprising transfecting amniocytes with at least one nucleic acid which brings about expression of the adenoviral gene products of the E1A region and E1B region.

9. A process as claimed in claim 8, wherein the amniocytes are primary amniocytes.

10. A process as claimed in claim 9, wherein the primary amniocytes are human primary amniocytes.

11. A process as claimed in claim 8, wherein the nucleic acid is contained in an expression vector.

12. A process as claimed in claim 8, wherein expression of the gene product of the E1A region is under the control of a constitutive promoter and expression of the gene product of the E1A region is under the control of an adenoviral promoter.

13. A process as claimed in claim 12, wherein the constitutive promoter is the phosphoglycerate kinase (PGK) promoter.

14. A process as claimed in claim 12, wherein the adenoviral promoter is the E1B promoter.

15. A process as claimed in claim 8, wherein transfecting of the amniocytes or of the resulting cell line additionally brings about expression of the gene products of the adenovirus E2A, E2B, or E4 regions, or of Cre recombinase.

16. A process as claimed in claim 8, wherein the gene products of the adenovirus E1A region and E1B region are derived from human adenovirus type 5.

17. A permanent amniocytic cell line obtainable by the process as claimed in claim 8.

18. Permanent amniocytic cell line N52.E6 (DSM ACC2416).

19. A process for producing a gene transfer vector, the process comprising transfecting the gene transfer vector into a permanent amniocytic cell line comprising at least one nucleic acid which brings about expression of the gene products of the adenovirus E1A and E1B regions.

20. A process for producing an adenovirus mutant, the process comprising transfecting the adenovirus mutant into a permanent amniocytic cell line comprising at least one nucleic acid which brings about expression of the gene products of the adenovirus E1A and E1B regions.

21. The process of any of claim 19 or 20, wherein the process is used to produce an adenovirus vector, AAV (adeno-associated virus) vector, retrovirus vector, lentivirus vector, chimeric adenovirus-AAV vector, chimeric adenovirus-retrovirus vector, or chimeric adenovirus-lentivirus vector.

22. The process of claim 21, wherein the adenovirus vector is a first-generation adenovirus vector, second-generation adenovirus vector, adenovirus vector of large DNA capacity, or deleted adenovirus vector.

23. The process of any claim 19 or 20, wherein the process is used to produce a tropism-modified gene transfer vector or tropism-modified adenovirus mutant.

24. The process of any claim 19 or 20, wherein the amniocytic cell line of claim 1.

* * * * *

UNITED STATES PATENT AND TRADEMARK OFFICE
CERTIFICATE OF CORRECTION

PATENT NO.   : 6,558,948 B1
DATED        : May 6, 2003
INVENTOR(S)  : Kochanek et al.

It is certified that error appears in the above-identified patent and that said Letters Patent is hereby corrected as shown below:

Column 2,
Line 27, replace "necessry" with -- necessary --.

Column 3,
Line 3, replace "vi vo" with -- vivo --.

Column 4,
Line 7, replace "loxp" with -- loxP --.

Column 5,
Line 61, replace "unsucessfully" with -- unsuccessfully --.

Column 6,
Line 53, replace "heptatitis" with -- hepatitis --.

Column 8,
Line 35, replace "herefore" with -- therefore --.

Column 14,
Line 40, replace "a E4" with -- an E4 --.

Column 21,
Line 23, replace "BamHl." with -- BamHI --; and
Line 44, replace "isolat #34" with -- isolate #34 --.

Signed and Sealed this

Twenty-first Day of June, 2005

JON W. DUDAS
*Director of the United States Patent and Trademark Office*